(12) United States Patent
Koenemann et al.

(10) Patent No.: US 7,910,736 B2
(45) Date of Patent: Mar. 22, 2011

(54) METHOD FOR PRODUCING ORGANIC FIELD-EFFECT TRANSISTORS

(75) Inventors: Martin Koenemann, Mannheim (DE); Peter Erk, Frankenthal (DE); Zhenan Bao, Stanford, CA (US); Mang-Mang Ling, Santa Clara, CA (US)

(73) Assignees: BASF Aktiengesellschaft, Ludwigshafen (DE); The Board of Trustees of the Lenand Stanford Junior University, Palo Alto, CA (US)

( * ) Notice: Subject to any disclaimer, the term of this patent is extended or adjusted under 35 U.S.C. 154(b) by 874 days.

(21) Appl. No.: 11/744,611

(22) Filed: May 4, 2007

(65) Prior Publication Data

US 2008/0017850 A1   Jan. 24, 2008

Related U.S. Application Data

(63) Continuation-in-part of application No. 11/619,538, filed on Jan. 3, 2007, now abandoned, which is a continuation of application No. 11/417,149, filed on May 4, 2006, now abandoned, application No. 11/744,611, which is a continuation-in-part of application No. 11/550,229, filed on Oct. 17, 2006, now abandoned.

(51) Int. Cl.
*C07D 471/02* (2006.01)
*H01L 51/50* (2006.01)
*H01L 31/112* (2006.01)

(52) U.S. Cl. .............. 546/37; 313/504; 257/27
(58) Field of Classification Search .......... 546/37; 437/29; 257/27; 313/504
See application file for complete search history.

(56) References Cited

U.S. PATENT DOCUMENTS

| | | | |
|---|---|---|---|
| 4,667,036 A | 5/1987 | Iden et al. | |
| 5,986,099 A | 11/1999 | Mullen et al. | |
| 6,143,905 A | 11/2000 | Bohm et al. | |
| 6,184,378 B1 * | 2/2001 | Bohm et al. | 546/37 |
| 6,326,494 B1 | 12/2001 | Bohm et al. | |
| 2003/0153005 A1 | 8/2003 | Schmid et al. | |
| 2003/0181721 A1 | 9/2003 | Wurthner et al. | |
| 2005/0017237 A1 | 1/2005 | Ong et al. | |
| 2005/0176970 A1 | 8/2005 | Marks et al. | |
| 2005/0222416 A1 | 10/2005 | Bohm et al. | |
| 2007/0190783 A1 | 8/2007 | Gomez et al. | |
| 2007/0269924 A1 | 11/2007 | Gomez et al. | |
| 2009/0236591 A1 | 9/2009 | Konemann et al. | |

FOREIGN PATENT DOCUMENTS

| | | |
|---|---|---|
| DE | 32 35 526 A1 | 3/1984 |
| DE | 34 34 059 A1 | 3/1985 |
| DE | 195 47 209 A1 | 6/1997 |
| DE | 101 48 172 A1 | 4/2003 |
| JP | 7-295260 | 11/1995 |

OTHER PUBLICATIONS

U.S. Appl. No. 12/666,127, filed Dec. 22, 2009, Koenemann et al.
U.S. Appl. No. 12/673,908, filed Feb. 17, 2010, Koenemann, et al.
U.S. Appl. No. 12/738,947, filed Apr. 20, 2010, Koenemann, et al.
Heinz Langhals, et al., "Novel Fluorescent Dyes by the Extension of the Core of Perylenetetracarboxylic Bismides", Eur. J. Org. Chem., 2000, pp. 365-380. Liqiang Fan, et al., "1,6-Disubstituted perylene bisimides: concise synthesis and characterization as near-infrared fluorescent dyes", Tetrahedron Letters, 46, 2005, pp. 4443-4447.

(Continued)

*Primary Examiner* — Charanjit S Aulakh
(74) *Attorney, Agent, or Firm* — Oblon, Spivak, McClelland, Maier & Neustadt, L.L.P.

(57) ABSTRACT

A method for producing an organic field-effect transistor, comprising the steps of:

a) providing a substrate comprising a gate structure, a source electrode and a drain electrode located on the substrate, and b) applying an n-type organic semiconducting compound to the area of the substrate where the gate structure, the source electrode and the drain electrode are located, wherein the n-type organic semiconducting compound is selected from the group consisting of compounds of the formula I

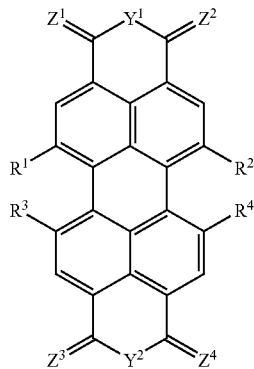

wherein $R^1$, $R^2$, $R^3$ and $R^4$ are independently hydrogen, chlorine or bromine, with the proviso that at least one of these radicals is not hydrogen, $Y^1$ is O or $NR^a$, wherein $R^a$ is hydrogen or an organyl residue, $Y^2$ is O or $NR^b$, wherein $R^b$ is hydrogen or an organyl residue, $Z^1$, $Z^2$, $Z^3$ and $Z^4$ are O, where, in the case that $Y^1$ is $NR^a$, one of the residues $Z^1$ and $Z^2$ may be a $NR^c$ group, where $R^a$ and $R^c$ together are a bridging group having 2 to 5 atoms between the terminal bonds, where, in the case that $Y^2$ is $NR^b$, one of the residues $Z^3$ and $Z^4$ may be a $NR^d$ group, where $R^b$ and $R^d$ together are a bridging group having 2 to 5 atoms between the terminal bonds.

13 Claims, 6 Drawing Sheets

OTHER PUBLICATIONS

Wenfeng Qiu, et al., "Suzuki Coupling Reaction of 1, 6, 7, 12-Tetrabromoperylene Bisimide", Organic Letters, vol. 8, No. 5, 2006, pp. 867-870.

Michael J. Ahrens, et al., "Cyanated Perylene-3, 4-dicaraboximides and Perylene-3, 4:9, 10-bis (discarboximide): Facile Chromophoric Oxidants for Organic Photonics and Electronics", Chem., Mater., 15, 2003, 2684-2686.

Brooks, A. Jones, et al., "High-Mobility Air-Stable n-Type Semiconductors with Processing Versatility: Dicyanoperylene-3,4:9, 10—bis(dicarboximides)", Angew, Chem., 116, 2004, pp. 6523-6526.

Zhijian Chen, et al., "Tetrachloro-substituted Perylene Bisimide Dyes as Promising n-Type Organic Semiconductors: Studies on Structural, Electrochemical and Charge Transport Properties", Chem., Phys., Chem., 5, 2004, pp. 137-140.

Michael G. Debije, et al., "Dramatic increase in charge carrier lifetime in a liquid crystalline perylene bisimide derivative upon bay substituation wit chlorine", Journal of Material Chemistry, 15, 2005, pp. 1270-1276.

Harald Graaf, et al., "Consequesnce of twisting the aromatic core of N, N'-dimethylperylene-3, 4, 9, 10-biscarboximide by chemical substituation for the electronic coupling and electric transport in thin films", Organic Electronics, 5, 2004, pp. 237-249.

U.S. Appl. No. 11/480,879, filed Jul. 6, 2006, Koenemann, et al.
U.S. Appl. No. 11/835,006, filed Aug. 7, 2007, Koenemann, et al.

* cited by examiner

TC-PTCDI: 1,6,7,12-tetrachloroperylentetracarboxylic diimide curve marked with x's represents the to-hysteresis loop
unmarked curve represents the back hysteresis loop

METHOD FOR PRODUCING ORGANIC FIELD-EFFECT TRANSISTORS

BACKGROUND OF THE INVENTION

1. Field of the Invention

The present invention relates to a method for producing an organic field-effect transistor.

2. Description of the Related Art

In the field of microelectronics there is a constant need to develop smaller device elements that can be reproduced conveniently and inexpensively at a lowest possible failure rate. Modern digital integrated circuits are based on field-effect transistors (FET), which rely on an electric field to control the conductivity of a "channel" in a semiconductor material. Organic field-effect transistors (OFET) allow the production of flexible or unbreakable substrates for integrated circuits having large active areas. As OFETs enable the production of complex circuits, they have a wide area of potential application (e.g. in driver circuits of pixel displays).

Methods for the manufacture of integrated circuits (IC) are well known in the art, e.g. by lithographic techniques.

DE-A-32 35 526 discloses perylene-3,4,9,10-tetracarboxylic diimides, which are substituted on the perylene nucleus with at least one group selected from among alkoxy, alkylthio, aryloxy, arylthio, =$SO_2$ and —$SO_2$—R groups. In addition, they may be substituted on the perylene nucleus with at least one chlorine or bromine group.

DE-A-34 34 059 discloses chlorinated perylenetetracarboxylic diimides prepared by chlorinating perylenetetracarboxylic diimides with sulfuryl chloride in an inert organic liquid in the presence of a catalyst. The perylene nucleus bears 2, 3, 4 or 5 or 6 chlorine groups. The substituents of the diimide nitrogen atoms are, independently of one another, either a) straight-chain or branched $C_1$-$C_{18}$-alkyl which is unsubstituted or substituted by cyano, hydroxyl, cycloalkyl, alkylcarbonyloxy, alkenylcarbonyloxy or cycloalkylcarbonyloxy and in which the alkyl chain may also be interrupted by O or S, or b) $C_5$-$C_{18}$-cycloalkyl, which is unsubstituted or substituted by alkyl, carboalkoxy or trifluoromethyl.

DE-A-195 47 209 discloses 1,7-disubstituted perylene-3,4,9,10-tetracarboxylic dianhydrides and perylene-3,4,9,10-tetracarboxylic acids where the substituents are selected from among substituted or unsubstituted aryloxy, arylthio, hetaryloxy or hetarylthio. Also disclosed are 1,7-dibromoperylene-3,4,9,10-tetracarboxylic diimides as intermediates for these compounds.

U.S. Pat. No. 5,986,099 discloses substituted quaterrylenetetracarboxylic diimides, wherein the aromatic nucleus can bear up to 12 substituents, *inter alia* halogen.

US 2005/0222416 A1 discloses 1,6,9,14-tetrasubstituted terylentetracarboxylic diimides wherein the substituents are *inter* alia bromine.

DE-A-101 48 172 describes fluorescent 2,6-substituted naphthalene-1,4,5,8-tetracarboxylic diimides, wherein the substituents are independently hydrogen, halogen, amino, —NHR or —OR, at least one of the substituents being different from hydrogen or halogen. Also disclosed are 2,6-dichloro-naphthalene-1,4,5,8-tetracarboxylic diimide and 2,6-dibromo-naphthalene-1,4,5,8-tetracarboxylic diimide that are employed as intermediates. The disclosed naphthalene-1,4,5,8-tetracarboxylic diimides are used *inter alia* as fluorescent dyes and laser dyes.

H. Langhals and S. Kirner disclose in Eur. J. Org. Chem. 2000, 365-380 fluorescent dyes on the basis of core-extended perylenetetracarboxylic bisimides. The only concrete halogen-substituted compound disclosed is 1-bromo-N,N'-bis(1-hexylheptyl)perylene-3,4,9,10-bis(dicarboximide).

H. Tian discloses in Tet. Let. 46, 2005, 4443-4447 the bromination of perylenetetracarboxylicbisanhdride yielding the tetrabromo derivative. Regarding the corresponding tetrabromodiimide no isolation and characterization is described.

D. Zhu discloses in Org. Let. 2006, 8, 5, 867 the corresponding tetrabromoperylenediimide with ethylhexyl substituents.

None of the aforementioned literature references describes the use of derivatives of rylene tetracarboxylic acids as n-type organic semiconductors for the production of OFETs.

M. J. Ahrens, M. J. Fuller and M. R. Wasielewski, Chem. Mater. 2003, 15, pages 2684-2686, disclose cyanated perylene-3,4-dicarboximides and perylene-3,4,9,10-bis(dicarboximide) as facile chromophoric oxidants for organic photonics and electronics.

B. A. Jones et al., Angew. Chem. 2004, 116, pages 6523-6526, describes dicyano-perylene-3,4,9,10-bis(dicarboximides) as high-mobility air-stable n-type semiconductors.

US 2005/0176970 A1 discloses the use of perylene-3,4-dicarboximides and perylene-3,4,9,10-bis(dicarboximide) with one or more electron-withdrawing moieties or groups as n-type semiconductors. Compounds with bromine substituents on the perylene nucleus are only employed as intermediates in the synthesis of the target molecules.

The compounds employed as n-type semiconductors according to the three last-mentioned literature documents do not bear halogen substituents.

Chem Phys Chem 2004, 5, 137-140 describes studies on structural, electrochemical and charge transport properties of tetrachloro-substituted perylene bisimides of the formula

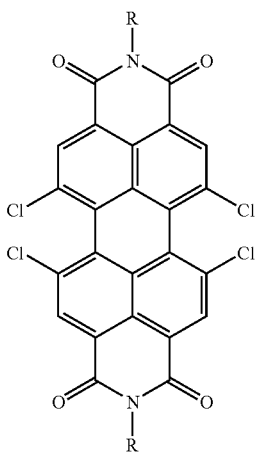

where R=n-$C_{12}H_{25}$, 4-(n-$C_{12}H_{25}$)$C_6H_4$, 2,6-(i-$C_3H_7$)$_2C_6H_3$. This document does not teach a method for the production of OFETs.

J. Mater. Chem., 2005, 15, 1270-1276 (Wuerthner, Muellen et al.), reports on an increase in charge carrier lifetime in a liquid crystalline perylene bisimide derivative upon substitution of the aromatic nucleus with chlorine. The employed perylene bisimide derivative has the following structure

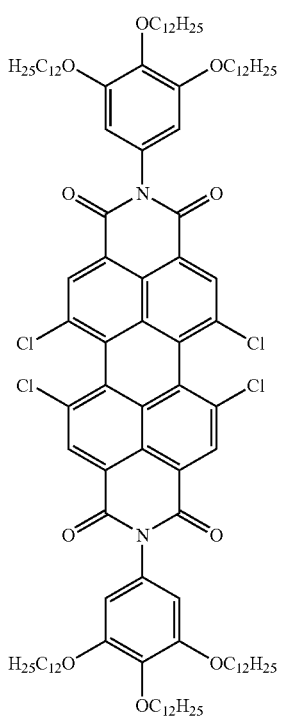

This document also does not teach a method for the production of OFETs.

US 2005/0017237 describes electronic devices including a semiconductor layer on the basis of compounds of the rylene type. The only concrete example of a thin film transistor comprises a perylenetetracarboxylic diimide with unsubstituted aromatic core.

US 2003/0181721 A1 (Wuerthner) discloses tetra-substituted perylenetetracarboxylic diimides of the formula

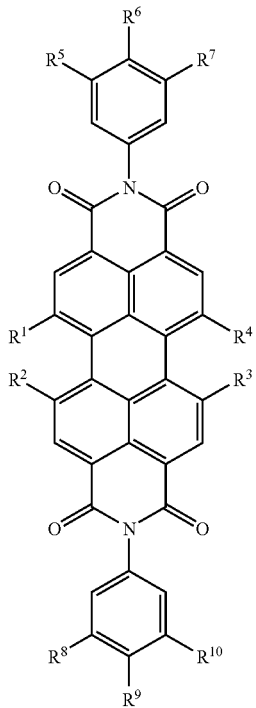

where $R^1$, $R^2$, $R^3$ and $R^4$ are independently hydrogen, chlorine, bromine, substituted or unsubstituted aryloxy, arylthio, arylamino, hetaryloxy or hetarylthio, $R^5$, $R^6$, $R^7$, $R^8$, $R^9$ and $R^{10}$ are independently hydrogen or long-chain alkyl, alkoxy or alkylthio with the proviso that at least four of these radicals are not hydrogen.

It is also mentioned in very general terms that such perylimides are useful for electronics, optoelectronics and photonic applications such as charge transport materials in luminescent diodes and photovoltaic diodes, photoconductors and transistors. This document also does not teach a method for the production of OFETs. The only concrete halogen-substituted compounds disclosed have aromatic nuclei substituted by four chlorine radicals or four bromine radicals and they are only used as intermediates in the synthesis of the target molecules.

D. Schlettwein et al compares in Organic Electronics 5 (2004), 237-249 the electrical properties of thin films of 1,6,7,12-tetrachloro-N,N'-dimethylperylene-3,4,9,10-biscarboximide prepared by physical vapour deposition with those of the corresponding unchlorinated compound. The specific conductivity of thin films of the unchlorinated substrate is about 100 times higher than that of the unchlorinated compound.

SUMMARY OF THE INVENTION

In a first aspect, the invention provides a method for producing an organic-field effect transistor, comprising the steps of:

a) providing a substrate comprising a gate structure, a source electrode and a drain electrode located on the substrate, and b) applying an n-type organic semiconducting compound to the area of the substrate where the gate structure, the source electrode and the drain electrode are located, wherein the n-type organic semiconducting compound is selected from compounds of the formula I

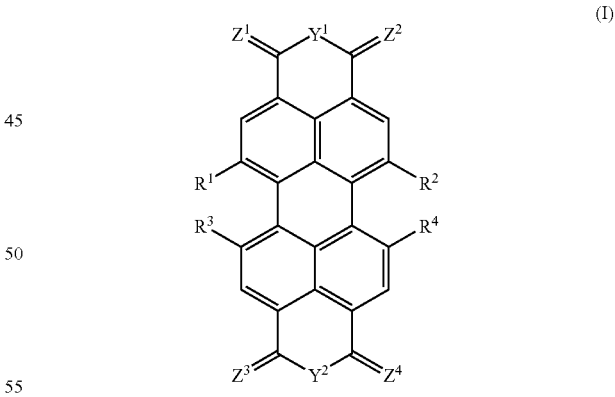

wherein $R^1$, $R^2$, $R^3$ and $R^4$ are independently hydrogen, chlorine or bromine, with the proviso that at least one of these radicals is not hydrogen, $Y^1$ is O or $NR^a$, wherein $R^a$ is hydrogen or an organyl residue, $Y^2$ is O or $NR^b$, wherein $R^b$ is hydrogen or an organyl residue, $Z^1$, $Z^2$, $Z^3$ and $Z^4$ are O, where, in the case that $Y^1$ is $NR^a$, one of the residues $Z^1$ and $Z^2$ may be a $NR^c$ group, where $R^a$ and $R^c$ together are a bridging group having 2 to 5 atoms between the terminal bonds, where, in the case that $Y^2$ is $NR^b$, one of the residues $Z^3$ and $Z^4$ may be a $NR^d$ group, where $R^b$ and $R^d$ together are a bridging group having 2 to 5 atoms between the terminal bonds.

In a further aspect, the invention provides a method for producing a substrate comprising a pattern of organic field-effect transistors, comprising the step of depositing on the surface of the substrate at least one compound (C1) capable of binding to the surface of the substrate and of binding at least one organic semiconducting compound (S) of the formula I and/or at least one compound (C2) capable of binding to the surface of the substrate and preventing the binding of at least one organic semiconducting compounds (S) of the formula I.

In a further aspect the invention provides a method for producing a substrate comprising a pattern of organic field-effect transistors, each transistor comprising:
   an organic semiconductor (S) located on the substrate;
   a gate structure positioned to control the conductivity of a channel portion of the crystallite; and
   conductive source and drain electrodes located at opposite ends of the channel portion,
wherein at least one organic semiconducting compound (S) of the formula I is applied to the surface of the substrate to enable at least a portion of the applied organic semiconducting compound (S) to bind to at least a portion of the binding sites on the surface of the substrate.

In a further aspect, the invention provides a method for producing an electronic device comprising the step of providing on a substrate a pattern of organic field-effect transistors, wherein at least part of the transistors comprise at least one compound of the formula (I) as n-type organic semiconducting compound.

In a further aspect, the invention provides an electronic device comprising on a substrate a pattern of organic field-effect transistors, wherein at least part of the transistors comprise at least one compound of the formula (I) as n-type organic semiconducting compound.

The method according to the invention can be used to provide a wide variety of devices. Such devices may include electrical devices, optical devices, optoelectronic devices (e.g. semiconductor devices for communications and other applications such as light emitting diodes, electroabsorptive modulators and lasers), mechanical devices and combinations thereof. Functional devices assembled from transistors obtained according to the method of the present invention may be used to produce various IC architectures. Further, at least one compound of the formula (I) may be employed in conventional semiconductor devices, such as diodes, light-emitting diodes (LEDs), inverters, sensors, and bipolar transistors. One aspect of the present invention includes the use of the method of the invention to fabricate an electronic device from adjacent n-type and/or p-type semiconducting components. This includes any device that can be made by the method of the invention that one of ordinary skill in the art would desirably make using semiconductors. Examples of such devices include, but are not limited to, field effect transistors (FETs), bipolar junction transistors (BJTs), tunnel diodes, modulation doped superlattices, complementary inverters, light-emitting devices, light-sensing devices, biological system imagers, biological and chemical detectors or sensors, thermal or temperature detectors, Josephine junctions, nanoscale light sources, photodetectors such as polarization-sensitive photodetectors, gates, inverters, AND, NAND, NOT, OR, TOR, and NOR gates, latches, flip-flops, registers, switches, clock circuitry, static or dynamic memory devices and arrays, state machines, gate arrays, and any other dynamic or sequential logic or other digital devices including programmable circuits.

A special type of electronic device in an inverter. In digital logic an inverter is a logic gate which inverts the digital signal driven on its input. It is also called NOT gate. The truth table of the gate is as follows: input 0=output 1; input 1=output 0. In practice, an inverter circuit outputs a voltage representing the opposite logic-level as its input. Digital electronics are circuits that operate at fixed voltage levels corresponding to a logical 0 or 1. An inverter circuit serves as the basic logic gate to swap between those two voltage levels. Implementation determines the actual voltage, but common levels include (0, +5V) for TTL circuits. Common types include resistive-drain, using one transistor and one resistor; and CMOS (complementary metal oxide semiconductor), which uses two (opposite type) transistors per inverter circuit. The performance quality of a digital inverter can be measured using the Voltage Transfer Curve (VTC), i.e. a plot of input vs. output voltage. From such a graph, device parameters including noise tolerance, gain, and operating logic-levels can be obtained. Ideally, the voltage transfer curve (VTC) appears as an inverted step-function (i.e. precise switching between on and off) but in real devices, a gradual transition region exists. The slope of this transition region is a measure of quality: the steeper (close to infinity) the slopes the more precise the switching. The tolerance to noise can be measured by comparing the minimum input to the maximum output for each region of operation (on/off). The output voltage VOH can be a measure of signal driving strength when cascading many devices together. The digital inverter is considered the base building block for all digital electronics. Memory (1 bit register) is built as a latch by feeding the output of two serial inverters together. Multiplexers, decoders, state machines, and other sophisticated digital devices all rely on inverter.

In a further aspect the invention provides an inverter comprising at least one compound of the formula I as n-type organic semiconducting compound. A special embodiment are CMOS inverter comprising two (opposite type) transistors. For high speed CMOS circuits, it is highly desirable that both p- and n-channel semiconductors have similar good mobilities. For p-channel transistors, there are a number of candidates with mobility greater than 0.1 cm$^2$/Vs, e.g. pentacene. Now it was surprisingly found that the compounds of the formula I can be advantageously employed as n-type semiconductors in inverters.

In a further aspect the invention provides a method for producing an integrated circuit (IC) comprising a substrate comprising a pattern of organic field-effect transistors, each transistor comprising at least one organic semiconducting compound (S) of the formula I located on the substrate, wherein the at least one organic semiconducting compound (S) of the formula I is applied to the surface of the substrate to enable at least a portion of the applied organic semiconducting compound (S) to bind to at least a portion of the binding sites on the surface of the substrate.

In a further aspect the invention provides the use of compounds of the formula I as n-type semiconductors. They are especially advantageous as n-type semiconductors for organic field-effect transistors, organic solar cells and organic light-emitting diodes (OLEDs).

In a further aspect the invention provides a method for preparing a compound of the formula I.

In a further aspect the invention provides novel compounds of the formula I.

In a further aspect the invention provides a method for producing a crystalline n-type organic semiconducting compound, wherein a compound of the formula I is subjected to a chemical vapor transport (CVT).

DETAILED DESCRIPTION OF PREFERRED EMBODIMENTS OF THE INVENTION

Figure 1:
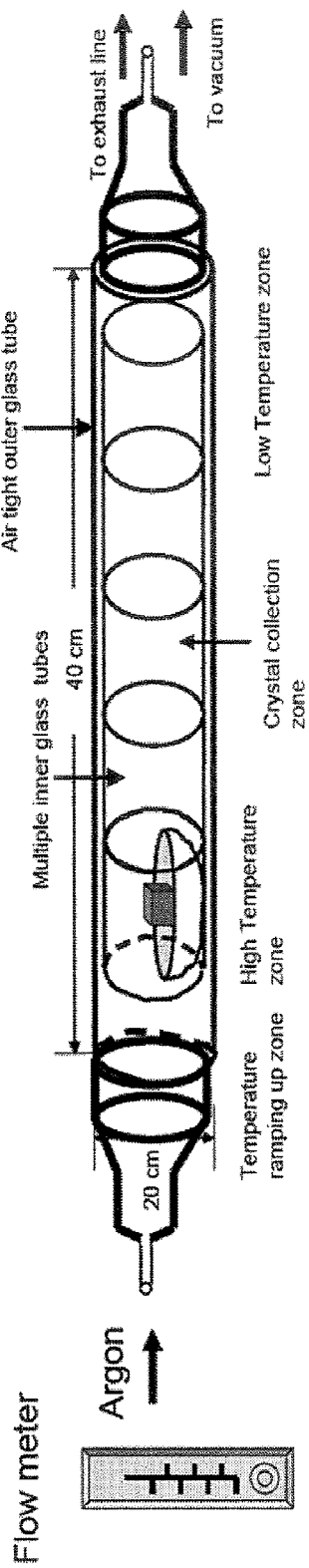
FIG. 1 shows an apparatus for the purification of organic semiconducting compounds by physical vapor transport. The apparatus according to FIG. 1 is suitable to prepare single crystals of the organic semiconducting compounds.

For the purposes of the present invention, the term "alkyl" embraces straight-chain and branched alkyl groups. These groups are preferably straight-chain or branched $C_1$-$C_{30}$-alkyl groups, more preferably $C_1$-$C_{20}$-alkyl groups, particularly preferably $C_1$-$C_{12}$-alkyl groups. Examples of alkyl groups are, in particular, methyl, ethyl, n-propyl, isopropyl, n-butyl, isobutyl, sec-butyl, tert-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

The expression "alkyl" also embraces alkyl groups whose carbon chain may be interrupted by one or more nonadjacent groups selected from among —O—, —S—, —$NR^e$—, —CO— and/or —$SO_2$—, where $R^e$ is preferably hydrogen, alkyl, cycloalkyl, heterocycloalkyl, aryl or hetaryl.

The expression "alkyl" also embraces substituted alkyl groups. Substituted alkyl groups can generally bear one or more than one (e.g. 1, 2, 3, 4, 5 or more than 5) substituents. The substituents are preferably selected from among cycloalkyl, heterocycloalkyl, aryl, hetaryl, halogen, hydroxy, mercapto, COOH, carboxylate, $SO_3H$, sulfonate, $NE^1E^2$, nitro and cyano, wherein $E^1$ and $E^2$ are, independently of one another, hydrogen, alkyl, cycloalkyl, heterocycloalkyl, aryl or hetaryl. Carboxylate is a derivative of a carboxylic acid function, in particular a metal carboxylate, a carboxylic ester function or a carboxamide function. Sulfonate is a derivative of a sulfonic acid function, in particular a metal sulfonate, a sulfonic acid ester function or a sulfonamide function. Cycloalkyl, heterocycloalkyl, aryl and hetaryl substituents of the alkyl group may their part be unsubstituted or substituted; suitable substituents are the substituents mentioned below for these groups.

The above statements regarding alkyl also apply to all alkyl moieties in alkoxy, alkyl-amino, alkylthio, alkylsulfinyl, alkylsulfonyl, etc.

Aryl-substituted alkyl ("arylalkyl") carries at least one unsubstituted or substituted aryl group as defined below. The alkyl moiety in "arylalkyl"can carry at least one further substituent and/or its carbon chain may be interrupted by one or more nonadjacent groups selected from among —O—, —S—, —$NR^e$—, —CO— and/or —$SO_2$—. Arylalkyl is preferably phenyl-$C_1$-$C_{10}$-alkyl, in particular phenyl-$C_1$-$C_4$-alkyl, e.g. benzyl, 1-phenethyl, 2-phenethyl, 1-phenprop-1-yl, 2-phenprop-1-yl, 3-phenprop-1-yl, 1-phenbut-1-yl, 2-phenbut-1-yl, 3-phenbut-1-yl, 4-phenbut-1-yl, 1-phenbut-2-yl, 2-phenbut-2-yl, 3-phenbut-2-yl, 4-phenbut-2-yl, 1-(phenmeth)-eth-1-yl, 1-(phenmethyl)-1-(methyl)-eth-1-yl or 1-(phenmethyl)-1-(methyl)-prop-1-yl; preferably benzyl or 2-phenethyl.

For the purposes of the present invention, alkenyl embraces straight-chain and branched alkenyl groups which, depending on chain length, may carry one or more double bonds (e.g. 1, 2, 3, 4 or more than 4). Preference is given to $C_2$-$C_{18}$ alkenyl groups, more preferably $C_2$-$C_{12}$ alkenyl groups. "Alkenyl" also embraces substituted alkenyl groups which can carry, for example, 1, 2, 3, 4, 5 or more than 5 substituents. Examples of suitable substituents include cycloalkyl, heterocycloalkyl, aryl, heteroaryl, halogen, hydroxy, mercapto, COOH, carboxylate, $SO_3H$, sulfonate, $NE^3E^4$, nitro and cyano, where $E^3$ and $E^4$ are, independently of one another, hydrogen, alkyl, cycloalkyl, heterocycloalkyl, aryl or hetaryl.

Examples of alkenyl are ethenyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, Penta-1,3-dien-1-yl, hexa-1,4-dien-1-yl, hexa-1,4-dien-3-yl, hexa-1,4-dien-6-yl, hexa-1,5-dien-1-yl, hexa-1,5-dien-3-yl, hexa-1,5-dien-4-yl, hepta-1,4-dien-1-yl, hepta-1,4-dien-3-yl, hepta-1,4-dien-6-yl, hepta-1,4-dien-7-yl, hepta-1,5-dien-1-yl, hepta-1,5-dien-3-yl, hepta-1,5-dien-4-yl, hepta-1,5-dien-7-yl, hepta-1,6-dien-1-yl, hepta-1,6-dien-3-yl, hepta-1,6-dien-4-yl, hepta-1,6-dien-5-yl, hepta-1,6-dien-2-yl, octa-1,4-dien-1-yl, octa-1,4-dien-2-yl, octa-1,4-dien-3-yl, octa-1,4-dien-6-yl, octa-1,4-dien-7-yl, octa-1,5-dien-1-yl, octa-1,5-dien-3-yl, octa-1,5-dien-4-yl, octa-1,5-dien-7-yl, octa-1,6-dien-1-yl, octa-1,6-dien-3-yl, octa-1,6-dien-4-yl, octa-1,6-dien-5-yl, octa-1,6-dien-2-yl, deca-1,4-dienyl, deca-1,5-dienyl, deca-1,6-dienyl, deca-1,7-dienyl, deca-1,8-dienyl, deca-2,5-dienyl, deca-2,6-dienyl, deca-2,7-dienyl, deca-2,8-dienyl, etc. The above remarks apply analogously to alkenyloxy, alkenylthio, etc.

For the purposes of the present invention, "alkynyl" embraces unsubstituted or substituted alkynyl groups which may carry one or more triple bonds. Preference is given to $C_2$-$C_{18}$ alkynyl groups, more preferably $C_2$-$C_{12}$ alkynyl groups. Examples of alkynyl are ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl, and the like. The above remarks apply analogously to alkynyloxy, alkynylthio, etc. "Alkynyl" also embraces substituted alkynyl groups, which can carry, for example, 1, 2, 3, 4, 5 or more than 5 radicals. Examples of suitable radicals for alkynyl are the same as those mentioned above as suitable radicals for "alkyl".

For the purposes of the present invention, the term "cycloalkyl" embraces both substituted and unsubstituted cycloalkyl groups, preferably $C_3$-$C_8$-cycloalkyl groups like cyclopropyl, cyclobutyl, cyclopentyl, cyclohexyl, cycloheptyl or cyclooctyl, in particular $C_5$-C8-cycloalkyl. Substituted cycloalkyl groups can carry, for example, 1, 2, 3, 4, 5 or more than 5 substituents which are preferably selected independently of alkyl and substituents as defined above for "alkyl". Substituted cycloalkyl groups carry preferably one or more, e.g. 1, 2, 3, 4 or 5, $C_1$-$C_6$-alkyl groups.

Examples of preferred cycloalkyl groups are cyclopentyl, 2- and 3-methylcyclopentyl, 2- and 3-ethylcyclopentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec.-butylcyclohexyl, 3- and 4-tert.-butylcyclohexyl, cycloheptyl, 2-, 3- and 4-methylcycloheptyl, 2-, 3- and 4-ethylcycloheptyl, 3- and 4-propylcycloheptyl, 3- and 4-isopropylcycloheptyl, 3- and 4-butylcycloheptyl, 3- and 4-sec.-butylcycloheptyl, 3- and 4-tert.-butylcycloheptyl, cyclooctyl, 2-, 3-, 4- and 5-methylcyclooctyl, 2-, 3-, 4- and 5-ethylcyclooctyl, 3-, 4- and 5-propylcyclooctyl.

The term "cycloalkenyl" embraces unsubstituted and substituted monounsaturated hydrocarbon groups having 3 to 8, preferably 5 to 6, carbon ring members, such as cyclopenten-1-yl, cyclopenten-3-yl, cyclohexen-1-yl, cyclohexen-3-yl, cyclohexen-4-yl and the like. Suitable substituents for cycloalkenyl are the same as those mentioned above for cycloalkyl.

The term "bicycloalkyl" preferably embraces bicyclic hydrocarbon groups having 5 to 10 carbon atoms such as bicyclo[2.2.1]hept-1-yl, bicyclo[2.2.1]hept-2-yl, bicyclo[2.2.1]hept-7-yl, bicyclo[2.2.2]oct-1-yl, bicyclo[2.2.2]oct-2-yl, bicyclo[3.3.0]octyl, bicyclo[4.4.0]decyl and the like.

For the purposes of the present invention, the term "aryl" embraces monocyclic or polycyclic aromatic hydrocarbon radicals which may be unsubstituted or unsubstituted. Aryl is preferably unsubstituted or substituted phenyl, naphthyl, indenyl, fluorenyl, anthracenyl, phenanthrenyl, naphthacenyl, chrysenyl, pyrenyl, etc., and in particular phenyl or naphthyl. Aryl, when substituted, may carry—depending on the number and size of the ring systems—one or more (e.g. 1, 2, 3, 4, 5 or more than 5) substituents which are preferably selected independently of one another from among alkyl, alkoxy, cycloalkyl, heterocycloalkyl, aryl, hetaryl, halogen, hydroxy, mercapto, COOH, carboxylate, $SO_3H$, sulfonate, $NE^5E^6$, nitro and cyano, where $E^5$ und $E^6$, independently of one another, are hydrogen, alkyl, cycloalkyl, heterocycloalkyl, aryl or hetaryl. Aryl is in particular phenyl which, when substituted, generally may carry 1, 2, 3, 4 or 5, preferably 1, 2 or 3, substituents.

Aryl, which may be unsubstituted or substituted, is preferably 2-, 3- und 4-methylphenyl, 2,4-, 2,5-, 3,5- and 2,6-dimethylphenyl, 2,4,6-trimethylphenyl, 2-, 3- and 4-ethylphenyl, 2,4-, 2,5-, 3,5- and 2,6-diethylphenyl, 2,4,6-triethylphenyl, 2-, 3- and 4-propylphenyl, 2,4-, 2,5-, 3,5- and 2,6-dipropylphenyl, 2,4,6-tripropylphenyl, 2-, 3- and 4-isopropylphenyl, 2,4-, 2,5-, 3,5- and 2,6-diisopropylphenyl, 2,4,6-triisopropylphenyl, 2-, 3- and 4-butylphenyl, 2,4-, 2,5-, 3,5- and 2,6-dibutylphenyl, 2,4,6-tributylphenyl, 2-, 3- and 4-isobutylphenyl, 2,4-, 2,5-, 3,5- and 2,6-diisobutylphenyl, 2,4,6-triisobutylphenyl, 2-, 3- and 4-sec-butylphenyl, 2,4-, 2,5-, 3,5- and 2,6-di-sec-butylphenyl, 2,4,6-tri-sec-butylphenyl, 2-, 3- and 4-tert.-butylphenyl, 2,4-, 2,5-, 3,5- and 2,6-di-tert.-butylphenyl and 2,4,6-tri-tert.-butylphenyl; 2-, 3- and 4-methoxyphenyl, 2,4-, 2,5-, 3,5- and 2,6-dimethoxyphenyl, 2,4,6-trimethoxyphenyl, 2-, 3- and 4-ethoxyphenyl, 2,4-, 2,5-, 3,5- and 2,6-diethoxyphenyl, 2,4,6-triethoxyphenyl, 2-, 3- and 4-propoxyphenyl, 2,4-, 2,5-, 3,5- and 2,6-dipropoxyphenyl, 2-, 3- and 4-isopropoxyphenyl, 2,4-, 2,5-, 3,5- and 2,6-diisopropoxyphenyl and 2-, 3- and 4-butoxyphenyl; 2-, 3- and 4-cyanophenyl.

For the purposes of the present invention heterocycloalkyl embraces nonaromatic, unsaturated or fully saturated, cycloaliphatic groups having generally 5 to 8 ring atoms, preferably 5 or 6 ring atoms, in which 1, 2 or 3 of the ring carbon atoms are replaced by heteroatoms selected from oxygen, nitrogen, sulfur, and a group —$NR^3$—, said cycloaliphatic groups further being unsubstituted or substituted by one or more—for example, 1, 2, 3, 4, 5 or 6—$C_1$-$C_6$ alkyl groups. Examples that may be given of such heterocycloaliphatic groups include pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, dihydrothien-2-yl, tetrahydrofuranyl, dihydrofuran-2-yl, tetrahydropyranyl, 1,2-oxazolin-5-yl, 1,3-oxazolin-2-yl, and dioxanyl.

For the purposes of the present invention heteroaryl embraces substituted or unsubstituted, heteroaromatic, monocyclic or polycyclic groups, preferably the groups pyridyl, quinolinyl, acridinyl, pyridazinyl, pyrimidinyl, pyrazinyl, pyrrolyl, imidazolyl, pyrazolyl, indolyl, purinyl, indazolyl, benzotriazolyl, 1,2,3-triazolyl, 1,3,4-triazolyl, and carbazolyl, which, when substituted, can carry generally 1, 2 or 3 substituents. The substituents are selected from $C_1$-$C_6$ alkyl, $C_1$-$C_6$ alkoxy, hydroxyl, carboxyl, halogen and cyano.

5- to 7-membered heterocycloalkyl or heteroaryl radicals bonded by a nitrogen atom and optionally containing further heteroatoms are, for example, pyrrolyl, pyrazolyl, imidazolyl, triazolyl, pyrrolidinyl, pyrazolinyl, pyrazolidinyl, imidazolinyl, imidazolidinyl, pyridinyl, pyridazinyl, pyrimidinyl, pyrazinyl, triazinyl, piperidinyl, piperazinyl, oxazolyl, isooxazolyl, thiazolyl, isothiazolyl, indolyl, quinolinyl, isoquinolinyl or quinaldinyl.

Halogen is fluorine, chlorine, bromine or iodine.

Concrete examples of residues $R^a$ and $R^b$ in the following formulae are:

methyl, ethyl, n-propyl, isopropyl, n-butyl, isobutyl, sec.-butyl, tert.-butyl, n-pentyl, n-hexyl, n-heptyl, n-octyl, n-nonyl, n-decyl, n-undecyl, n-dodecyl, n-tridecyl, n-tetradecyl, n-hexadecyl, n-octadecyl and n-eicosyl.

2-methoxyethyl, 2-ethoxyethyl, 2-propoxyethyl, 2-butoxyethyl, 3-methoxypropyl, 3-ethoxypropyl, 3-propoxypropyl, 3-butoxypropyl, 4-methoxybutyl, 4-ethoxybutyl, 4-propoxybutyl, 3,6-dioxaheptyl, 3,6-dioxaoctyl, 4,8-dioxanonyl, 3,7-dioxaoctyl, 3,7-dioxanonyl, 4,7-dioxaoctyl, 4,7-dioxanonyl, 2- and 4-butoxybutyl, 4,8-dioxadecyl, 3,6,9-trioxadecyl, 3,6,9-trioxaundecyl, 3,6,9-trioxadodecyl, 3,6,9,12-tetraoxatridecyl and 3,6,9,12-tetraoxatetradecyl;

2-methylthioethyl, 2-ethylthioethyl, 2-propylthioethyl, 2-butylthio-ethyl, 3-methylthiopropyl, 3-ethylthiopropyl, 3-propylthiopropyl, 3-butylthiopropyl, 4-methylthiobutyl, 4-ethylthiobutyl, 4-propylthiobutyl, 3,6-dithiaheptyl, 3,6-dithiaoctyl, 4,8-dithianonyl, 3,7-dithiaoctyl, 3,7-dithianonyl, 2- and 4-butylthiobutyl, 4,8-dithiadecyl, 3,6,9-trithiadecyl, 3,6,9-trithia-undecyl, 3,6,9-trithiadodecyl, 3,6,9,12-tetrathiatridecyl and 3,6,9,12-tetrathiatetradecyl;

2-monomethyl- and 2-monoethylaminoethyl, 2-dimethylaminoethyl, 2- and 3-dimethyl-aminopropyl, 3-monoisopropylaminopropyl, 2- and 4-monopropylaminobutyl, 2- and 4-dimethylaminobutyl, 6-methyl-3,6-diazaheptyl, 3,6-dimethyl-3,6-diazaheptyl, 3,6-di-azaoctyl, 3,6-dimethyl-3,6-diazaoctyl, 9-methyl-3,6,9-triazadecyl, 3,6,9-trimethyl-3,6,9-triazadecyl, 3,6,9-triazaundecyl, 3,6,9-trimethyl-3,6,9-triazaundecyl, 12-methyl-3,6,9,12-tetraazatridecyl and 3,6,9,12-tetramethyl-3,6,9,12-tetraazatridecyl;

(1-ethylethyliden)aminoethylen, (1-ethylethyliden)aminopropylen, (1-ethylethyliden)-aminobutylen, (1-ethylethyliden)aminodecylen and (1-ethylethyliden)aminododecylen;

propan-2-on-1-yl, butan-3-on-1-yl, butan-3-on-2-yl and 2-ethylpentan-3-on-1-yl;

2-methylsulfoxidoethyl, 2-ethylsulfoxidoethyl, 2-propylsulfoxidoethyl, 2-isopropylsulf-oxidoethyl, 2-butylsulfoxidoethyl, 2- and 3-methylsulfoxidopropyl, 2- and 3-ethylsulfoxidopropyl, 2- and 3-propylsulfoxidopropyl, 2- and 3-butylsulfoxidopropyl, 2- and 4-methylsulfoxidobutyl, 2- and 4-ethylsulfoxidobutyl, 2- and 4-propylsulfoxidobutyl and 4-butylsulfoxidobutyl;

2-methylsulfonylethyl, 2-ethylsulfonylethyl, 2-propylsulfonylethyl, 2-isopropylsulfonylethyl, 2-butylsulfonylethyl, 2- and 3-methylsulfonylpropyl, 2- and 3-ethylsulfonylpropyl, 2- and 3-propylsulfonylpropyl, 2- and 3-butylsulfonylproypl, 2- and 4-methylsulfonylbutyl, 2- and 4-ethylsulfonylbutyl, 2- and 4-propylsulfonylbutyl and 4-butylsulfonylbutyl;

carboxymethyl, 2-carboxyethyl, 3-carboxypropyl, 4-carboxybutyl, 5-carboxypentyl, 6-carboxyhexyl, 8-carboxyoctyl, 10-carboxydecyl, 12-carboxydodecyl and 14-carboxytetradecyl;

sulfomethyl, 2-sulfoethyl, 3-sulfopropyl, 4-sulfobutyl, 5-sulfopentyl, 6-sulfohexyl, 8-sulfooctyl, 10-sulfodecyl, 12-sulfododecyl and 14-sulfotetradecyl;

2-hydroxyethyl, 2- and 3-hydroxypropyl, 3- and 4-hydroxybutyl and 8-hydroxy-4-oxaoctyl;

2-cyanoethyl, 3-cyanopropyl, 3- and 4-cyanobutyl;

2-chloroethyl, 2- and 3-chloropropyl, 2-, 3- and 4-chlorobutyl, 2-bromoethyl, 2- and 3-bromopropyl and 2-, 3- and 4-bromobutyl;

2-nitroethyl, 2- and 3-nitropropyl and 2-, 3- and 4-nitrobutyl;

methoxy, ethoxy, propoxy, butoxy, pentoxy and hexoxy;

methylthio, ethylthio, propylthio, butylthio, pentylthio and hexylthio;

ethynyl, 1- and 2-propynyl, 1-, 2- and 3-butynyl, 1-, 2-, 3- and 4-pentynyl, 1-, 2-, 3-, 4- and 5-hexynyl, 1-, 2-, 3-, 4-, 5-, 6-, 7-, 8- and 9-decynyl, 1-, 2-, 3-, 4-, 5-, 6-, 7-, 8-, 9-, 10- and 11-dodecynyl and 1-, 2-, 3-, 4-, 5-, 6-, 7-, 8-, 9-, 10-, 11-, 12-, 13-, 14-, 15-, 16- and 17-octadecynyl;

ethenyl, 1- and 2-propenyl, 1-, 2- and 3-butenyl, 1-, 2-, 3- and 4-pentenyl, 1-, 2-, 3-, 4- and 5-hexenyl, 1-, 2-, 3-, 4-, 5-, 6-, 7-, 8- and 9-decenyl, 1-, 2-, 3-, 4-, 5-, 6-, 7-, 8-, 9-, 10- and 11-dodecenyl and 1-, 2-, 3-, 4-, 5-, 6-, 7-, 8-, 9-, 10-, 11-, 12-, 13-, 14-, 15-, 16- and 17-octadecenyl;

methylamino, ethylamino, propylamino, butylamino, pentylamino, hexylamino, dicyclopentylamino, dicyclohexylamino, dicycloheptylamino, diphenylamino and dibenzylamino;

formylamino, acetylamino, propionylamino and benzoylamino;

carbamoyl, methylaminocarbonyl, ethylaminocarbonyl, propylaminocarbonyl, butyl-aminocarbonyl, pentylaminocarbonyl, hexylaminocarbonyl, heptylaminocarbonyl, octylaminocarbonyl, nonylaminocarbonyl, decylaminocarbonyl and phenylamino-carbonyl;

aminosulfonyl, n-dodecylaminosulfonyl, n,n-diphenylaminosulfonyl, and n,n-bis(4-chlorophenyl)aminosulfonyl;

methoxycarbonyl, ethoxycarbonyl, propoxycarbonyl hexoxycarbonyl, dodecyloxycarbonyl, octadecyloxycarbonyl, phenoxycarbonyl, (4-tert-butyl-phenoxy)carbonyl and (4-chlorophenoxy)carbonyl;

methoxysulfonyl, ethoxysulfonyl, propoxysulfonyl, butoxysulfonyl, hexoxysulfonyl, dodecyloxysulfonyl, octadecyloxysulfonyl, phenoxysulfonyl, 1- and 2-naphthyloxysulfonyl, (4-tert.-butyiphenoxy)-sulfonyl and (4-chlorophenoxy)sulfonyl;

diphenylphosphino, di-(o-tolyl)phosphino and diphenylphosphinoxido;

fluoroine, chloroine, bromoine and iodoine;

phenylazo, 2-napthylazo, 2-pyridylazo and 2-pyrimidylazo;

cyclopropyl, cyclobutyl, cyclopentyl, 2- and 3-methylcyclopentyl, 2- and 3-ethylcyclo-pentyl, cyclohexyl, 2-, 3- and 4-methylcyclohexyl, 2-, 3- and 4-ethylcyclohexyl, 3- and 4-propylcyclohexyl, 3- and 4-isopropylcyclohexyl, 3- and 4-butylcyclohexyl, 3- and 4-sec.-butylcyclohexyl, 3- and 4-tert.-butylcyclohexyl, cycloheptyl, 2-, 3- and 4-methyl-cycloheptyl, 2-, 3- and 4-ethylcycloheptyl, 3- and 4-propylcycloheptyl, 3- and 4-iso-propylcycloheptyl, 3- and 4-butylcycloheptyl, 3- and 4-sec.-butylcycloheptyl, 3- and 4-tert.-butylcycloheptyl, cyclooctyl, 2-, 3-, 4- and 5-methylcyclooctyl, 2-, 3-, 4- and 5-ethylcyclooctyl and 3-, 4- and 5-propylcyclooctyl; 3- and 4-hydroxycyclohexyl, 3- and 4-nitrocyclohexyl and 3- and 4-chlorocyclohexyl;

1-, 2- and 3-cyclopentenyl, 1-, 2-, 3- and 4-cyclohexenyl, 1-, 2- and 3-cycloheptenyl and 1-, 2-, 3- and 4-cyclooctenyl;

2-dioxanyl, 4-morpholinyl, 4-thiomorpholinyl, 2- and 3-tetrahydrofuryl, 1-, 2- and 3-pyrrolidinyl, 1-piperazinyl, 2,5-piperazindion-1-yl and 1-, 2-, 3- and 4-piperidyl;

phenyl, 2-naphtyl, 2- and 3-pyrrolyl, 2-, 3- and 4-pyridyl, 2-, 4- and 5-pyrimidyl, 3-, 4- and 5-pyrazolyl, 2-, 4- and 5-imidazolyl, 2-, 4- and 5-thiazolyl, 3-(1,2,4-triazyl), 2-(1,3, 5-triazyl), 6-chinaldyl, 3-, 5-, 6- and 8-quinolinyl, 2-benzoxazolyl, 2-benzothiazolyl, 5-benzothiadiazolyl, 2- and 5-benzimidazolyl and 1- and 5-isoquinolyl;

1-, 2-, 3-, 4-, 5-, 6- and 7-indolyl, 1-, 2-, 3-, 4-, 5-, 6- and 7-isoindolyl, 5-(4-methyliso-indolyl), 5-(4-phenylisoindolyl), 1-, 2-, 4-, 6-, 7- and 8-(1,2,3,4-tetrahydroisoquinolinyl), 3-(5-phenyl)-(1,2,3,4-tetrahydroisoquinolinyl), 5-(3-dodecyl-(1,2,3,4-tetrahydroiso-quinolinyl), 1-, 2-, 3-, 4-, 5-, 6-, 7- and 8-(1,2,3,4-tetrahydroquinolinyl) and 2-, 3-, 4-, 5-, 6-, 7- and 8-chromanyl, 2-, 4- and 7-quinolinyl, 2-(4-phenylquinolinyl) and 2-(5-ethyl-quinolinyl);

2-, 3- and 4-methylphenyl, 2,4-, 3,5- and 2,6-dimethylphenyl, 2,4,6-trimethylphenyl, 2-, 3- and 4-ethylphenyl, 2,4-, 3,5- and 2,6-diethylphenyl, 2,4,6-triethylphenyl, 2-, 3- and 4-propylphenyl, 2,4-, 3,5- and 2,6-dipropylphenyl, 2,4,6-tripropylphenyl, 2-, 3- and 4-isopropylphenyl, 2,4-, 3,5- and 2,6-diisopropylphenyl, 2,4,6-triisopropylphenyl, 2-, 3- and 4-butylphenyl, 2,4-, 3,5- and 2,6-dibutylphenyl, 2,4,6-tributylphenyl, 2-, 3- and 4-isobutylphenyl, 2,4-, 3,5- and 2,6-diisobutylphenyl, 2,4,6-triisobutylphenyl, 2-, 3- and 4-sec.-butylphenyl, 2,4-, 3,5- and 2,6-di-sec.-butylphenyl and 2,4, 6-tri-sec.-butyl-phenyl; 2-, 3- and 4-methoxyphenyl, 2,4-, 3,5- and 2,6-dimethoxyphenyl, 2,4,6-tri-methoxyphenyl, 2-, 3- and 4-ethoxyphenyl, 2,4-, 3,5- and 2,6-diethoxyphenyl, 2,4,6-triethoxyphenyl, 2-, 3- and 4-propoxyphenyl, 2,4-, 3,5- and 2,6-dipropoxyphenyl, 2-, 3- and 4-isopropoxyphenyl, 2,4- and 2,6-diisopropoxyphenyl and 2-, 3- and 4-butoxyphenyl; 2-, 3- and 4-chlorophenyl and 2,4-, 3,5- and 2,6-dichlorophenyl; 2-, 3- and 4-hydroxyphenyl and 2,4-, 3,5- and 2,6-dihydroxyphenyl; 2-, 3- and 4-cyanophenyl; 3- and 4-carboxyphenyl; 3- and 4-carboxamidophenyl, 3- and 4-n-methylcarboxamido-phenyl and 3- and 4-n-ethylcarboxamidophenyl; 3- and 4-acetylaminophenyl, 3- and 4-propionylaminophenyl and 3- and 4-buturylaminophenyl; 3- and 4-n-phenylamino-phenyl, 3- and 4-n-(o-tolyl)aminophenyl, 3- and 4-n-(m-tolyl)aminophenyl and 3- and 4-(p-tolyl)aminophenyl; 3- and 4-(2-pyridyl)aminophenyl, 3- and 4-(3-pyridyl)amino-phenyl, 3- and 4-(4-pyridyl)aminophenyl, 3- and 4-(2-pyrimidyl)aminophenyl and 4-(4-pyrimidyl)aminophenyl;

4-phenylazophenyl, 4-(1-naphthylazo)phenyl, 4-(2-naphthylazo)phenyl, 4-(4-naphthyl-azo)phenyl, 4-(2-pyriylazo) phenyl, 4-(3-pyridylazo)phenyl, 4-(4-pyridylazo)phenyl, 4-(2-pyrimidylazo)phenyl, 4-(4-pyrimidylazo)phenyl and 4-(5-pyrimidylazo)phenyl;

phenoxy, phenylthio, 2-naphthoxy, 2-naphthylthio, 2-, 3- and 4-pyridyloxy, 2-, 3- and 4-pyridylthio, 2-, 4- and 5-pyrimidyloxy and 2-, 4- and 5-pyrimidylthio.

Preferred residues $R^a$ and $R^b$ containing fluorine are the following:

2,2,2-Trifluoroethyl, 2,2,3,3,3-pentafluoropropyl, 2,2-difluoroethyl, 2,2,2-trifluoro-1-phenylethylamin, 1-Benzyl-2,2, 2-trifluoroethyl, 2-bromo-2,2-difluoroethyl, 2,2,2-trifluoro-1-pyridin-2-ylethyl, 2,2-difluoropropyl, 2,2,2-trifluoro-1-(4-methoxyphenyl)ethylamin, 2,2,2-trifluoro-1-phenylethylamin, 2,2-difluoro-1-phenylethylamin, 1-(4-bromo-phenyl)-2,2,2-trifluoroethyl, 3-bromo-3,3-difluoropropyl, 3,3,3-trifluoropropylamin, 3,3,3-trifluoro-n-propyl, 1H,1H,2H,2H-perfluorodecyl, 3-(perfluorooctyl)propyl, pentafluorophenyl, 2,3,5,6-tetrafluorophenyl, 4-cyano-(2,3,5,6)-tetrafluorophenyl, 4-carboxy-2,3,5,6-tetrafluorophenyl, 2,4-difluorophenyl, 2,4,5-trifluorophenyl, 2,4,6-trifluorophenyl, 2,5-difluorophenyl, 2-fluoro-5-nitrophenyl, 2-fluoro-5-trifluoromethylphenyl, 2-fluoro-5-methylphenyl, 2,6-difluorophenyl, 4-carboxamido-2,3,5,6-tetrafluorophenyl, 2-bromo-4,6-difluorophenyl, 4-bromo-2-fluorophenyl, 2,3-difluorophenyl, 4-chloro-2-fluorophenyl, 2,3,4-trifluorophenyl, 2-fluoro-4-iodphenyl, 4-bromo-2,3,5,6-tetrafluorophenyl, 2,3,6-trifluorophenyl, 2-bromo-3,4,6-trifluorophenyl, 2-bromo-4,5,6-trifluorophenyl, 4-bromo-2,6-difluorophenyl, 2,3,4,5-tetrafluorophenyl, 2,4-difluoro-6-nitrophenyl, 2-fluoro-4-nitrophenyl, 2-chloro-6-fluorophenyl, 2-fluoro-4-methylphenyl, 3-chloro-2,4-difluorophenyl, 2,4-dibromo-6-fluorophenyl, 3,5-dichloro-2,4-difluorophenyl, 4-cyano-1-fluorophenyl, 1-chloro-4-fluorophenyl, 2-fluoro-3-trifluoromethylphenyl, 2-trifluoromethyl-6-fluorophenyl, 2,3,4,6-tetrafluorophenyl, 3-chloro-2-fluorophenyl, 5-chloro-2-fluorophenyl, 2-bromo-4-chloro-6-fluorophenyl, 2,3-dicyano-4,5,6-trifluorophenyl, 2,4,5-trifluoro-3-carboxyphenyl, 2,3,4-trifluoro-6-carboxyphenyl, 2,3,5-trifluorophenyl, 4-trifluoromethy-l2,3,5,6-tetrafluorophenyl, 1-fluoro-5-carboxyphenyl, 2-chloro-4,6-difluorophenyl, 6-bromo-3-chloro-2,4-difluorophenyl, 2,3,4-trifluoro-6-nitrophenyl, 2,5-difluoro-4-cyanophenyl, 2,5-difluoro-4-trifluoromethylphenyl, 2,3-difluoro-6-nitrophenyl, 4-trifluoromethyl-2,3-difluorophenyl, 2-bromo-4,6-difuorophenyl, 4-bromo-2-fluorophenyl, 2-nitrotetrafluorophenyl, 2,2',3,3',4',5,5',6,6'-nonabiphenyl, 2-nitro-3,5,6-trifluorophenyl, 2-bromo-6-fluorophenyl, 4-chloro-2-fluoro-6-iodphenyl, 2-fluoro-6-carboxyphenyl, 2,4-difluoro-3-trifluorophenyl, 2-fluoro-4-trifluorophenyl, 2-fluoro-4-carboxyphenyl, 4-bromo-2,5-difluorophenyl, 2,5-dibromo-3,4,6-trifluorophenyl, 2-fluoro-5-methylsulphonylpenyl, 5-bromo-2-fluorophenyl, 2-fluoro-4-hydroxymethylphenyl, 3-fluoro-4-bromomethylphenyl, 2-nitro-4-trifluoromethylphenyl, 4-trifluoromethylphenyl, 2-bromo-4-trifluoromethylphenyl, 2-bromo-6-chloro-4-(trifluoromethyl)phenyl, 2-chloro-4-trifluoromethylphenyl, 3-nitro-4-(trifluoromethyl)phenyl, 2,6-dichloro-4-(trifluoromethyl)phenyl, 4-trifluorophenyl, 2,6-dibromo-4-(trifluoromethyl)phenyl, 4-trifluoromethyl2,3,5,6-tetrafluorophenyl, 3-fluoro-4-trifluoromethylphenyl, 2,5-difluoro-4-trifluoromethylphenyl, 3,5-difluoro-4-trifluoromethylphenyl, 2,3-difluoro-4-trifluoromethylphenyl, 2,4-bis(trifluoromethyl)phenyl, 3-chloro-4-trifluoromethylphenyl, 2-bromo-4,5-di(trifluoromethyl)phenyl, 5-chloro-2-nitro-4-(trifluoromethyl)phenyl, 2,4,6-tris(trifluoromethyl)phenyl, 3,4-Bis(trifluoromethyl)phenyl, 2-fluoro-3-trifluoromethylphenyl, 2-Iod-4-trifluoromethylphenyl, 2-nitro-4,5-bis(trifluoromethyl)phenyl, 2-methyl4-(trifluoromethyl)phenyl, 3,5-dichloro-4-(trifluoromethyl)phenyl, 2,3,6-trichloro-4-(trifluoromethyl)phenyl, 4-(trifluoromethyl)benzyl, 2-fluoro-4-(trifluoromethyl)benzyl, 3-fluoro-4-(trifluoromethyl)benzyl, 3-chloro-4-(trifluoromethyl)benzyl, 4-fluorophenethyl, 3-(trifluoromethyl)phenethyl, 2-chloro-6-fluorophenethyl, 2,6-dichlorophenethyl, 3-fluorophenethyl, 2-fluorophenethyl, (2-trifluoromethyl)phenethyl, 4-fluorophenethyl, 3-fluorophenethyl, 4-trifluoromethylphenethyl, 2,3-difluorophenethyl, 3,4-difluorophenethyl, 2,4-difluorophenethyl, 2,5-difluorophenethyl, 3,5-difluorophenethyl, 2,6-difluorophenethyl,4-(4-fluorophenyl)phenethyl, 3,5-di(trifluoromethyl)phenethyl, pentafluorophenethyl, 2,4-di(trifluoromethyl)phenethyl, 2-nitro-4-(trifluoromethyl)phenethyl, (2-fluoro-3-trifluoromethyl)phenethyl, (2-fluoro-5-trifluoromethyl)phenethyl, (3-fluoro-5-trifluoromethyl)phenethyl, (4-fluoro-2-trifluoromethyl)phenethyl, (4-fluoro-3-trifluoromethyl)phenethyl, (2-fluoro-6-trifluoromethyl)phenethyl, (2,3,6-trifluoro)phenethyl, (2,4,5-trifluoro)phenethyl, (2,4,6-trifluoro)phenethyl, (2,3,4-trifluoro)phenethyl, (3,4,5-trifluoro)phenethyl, (2,3,5-trifluoro)phenethyl, (2-chloro-5-fluoro)phenethyl, (3-fluoro-4-trifluoromethyl)phenethyl, (2-chloro-5-trifluoromethyl)phenethyl, (2-fluoro-3-chloro-5-trifluoromethyl)phenethyl, (2-fluoro-3-chloro)phenethyl, (4-fluoro-3-chloro)phenethyl, (2-fluoro-4-chloro)phenethyl, (2,3-difluoro-4-methyl)phenethyl-, 2,6-difluoro-3-chlorophenethyl, (2,6-difluoro-3-methyl)phenethyl, (2-trifluoromethyl-5-chloro)phenethyl, (6-chloro-2-fluoro-5-methyl)phenethyl, (2,4-dichloro-5-fluoro)phenethyl, 5-chloro-2-fluorophenethyl, (2,5-difluoro-6-chloro)phenethyl, (2,3,4,5-tetrafluoro)phenethyl, (2-fluoro-4-trifluoromethyl)phenethyl, 2,3-(difluoro-4-trifluoromethyl)phenethyl, (2,5-di(trifluoromethyl))phenethyl, 2-fluoro-3,5-dibromophenethyl, (3-fluoro-4-nitro)phenethyl, (2-bromo-4-trifluoromethyl)phenethyl, 2-(bromo-5-fluoro)phenethyl, (2,6-difluoro-4-bromo)phenethyl, (2,6-difluoro-4-chloro)phenethyl, (3-chloro-5-fluoro)phenethyl, (2-bromo-5-trifluoromethyl)phenethyl and the like.

According to a preferred embodiment a compound of the formula I is employed, where 1, 2, 3 or 4 of the residues of the residues $R^1$, $R^2$, $R^3$ and $R^4$ are chlorine.

According to a further preferred embodiment a compound of the formula I is employed, where $R^1$, $R^2$, $R^3$ and $R^4$ are chlorine.

According to a further preferred embodiment a compound of the formula I is employed, 1, 2, 3 or 4 of the residues $R^1$, $R^2$, $R^3$ and $R^4$ are bromine.

According to a further preferred embodiment a compound of the formula I is employed, $R^1$, $R^2$, $R^3$ and $R^4$ are bromine.

Especially preferred are compounds of the formulae:

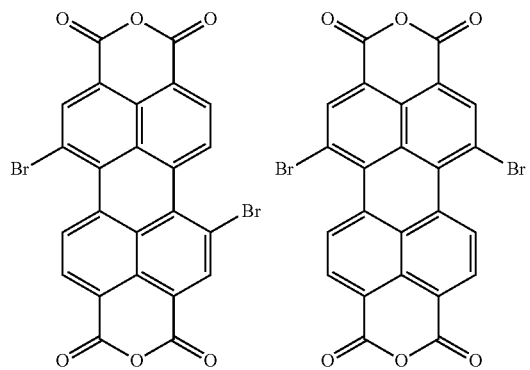

-continued

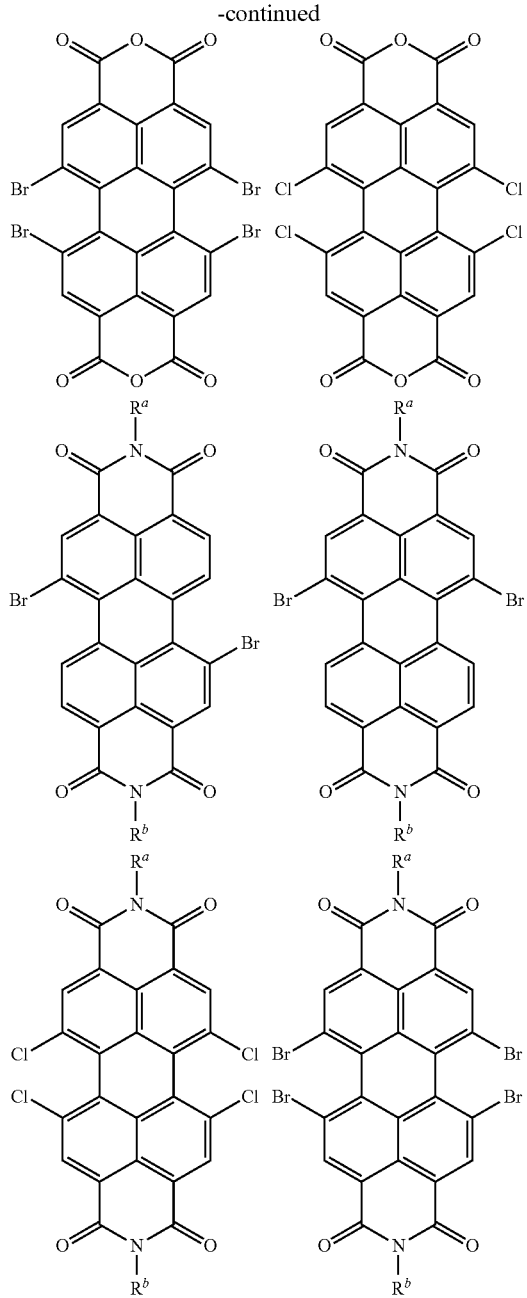

where $R^a$ and $R^b$ are independently hydrogen or unsubstituted or substituted alkyl, alkenyl, alkadienyl, alkynyl, cycloalkyl, bicycloalkyl, cycloalkenyl, heterocycloalkyl, aryl or hetaryl.

With regard to the meaning of residues $R^a$ and $R^b$ in the aforementioned compounds, reference is made to the definition provided at the beginning of the description.

Preferably, at least one of the residues $R^a$ and $R^b$ is an electron-withdrawing residue.

In a special embodiment at least one of the residues $R^a$ and $R^b$ is substituted once or more than once by fluorine. Preferred fluorine-substituted residues are the aforementioned.

In a further special embodiment $R^a$ and $R^b$ have the same meaning.

Further preferred embodiments are compounds of the formulae:

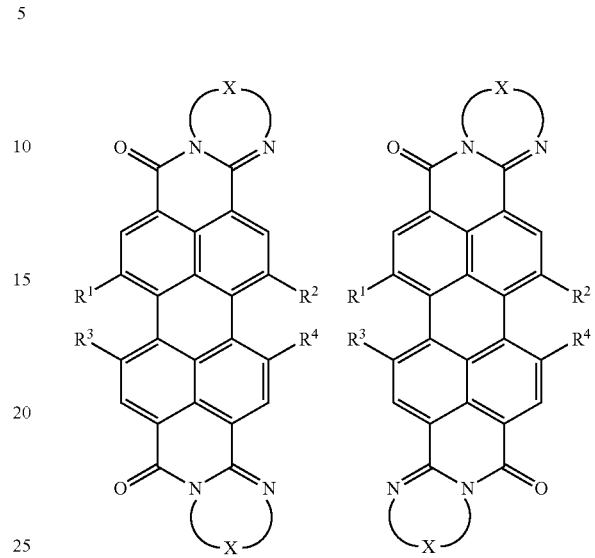

where $R^1$, $R^2$, $R^3$ and $R^4$ are defined as mentioned before,

X is a bridging group having 2 to 5 atoms between the terminal bonds.

Preferably, X, together with the N—C=N-group to which it is bound, forms a 5- to 8-membered heterocycle. The heterocycle can be part of a fused ring system having 1, 2 or 3 further rings that are selected from cycloalkyl, heterocycloalkyl, aryl and/or hetaryl. Fused-on rings are preferably unsubstituted or bear 1, 2, 3 or 4 substituents selected from among alkyl, alkoxy, cycloalkyl, aryl, halogen, hydroxy, mercapto, COOH, carboxylate, $SO_3H$, sulfonate, $NE^1E^2$, alkylene-$NE^1E^3$, nitro and cyano, where $E^1$ and $E^2$ independently are hydrogen, alkyl, cycloalkyl, heterocycloalkyl, aryl or hetaryl. X can bear 1, 2 or 3 substituents preferably selected from among unsubstituted or substituted alkyl, unsubstituted or substituted cycloalkyl and unsubstituted or substituted aryl, and/or X may be interrupted by one or more (e.g. 1, 2, 3 or more than 3) unsubstituted or substituted heteroatoms.

Preferably bridging group X is selected from among

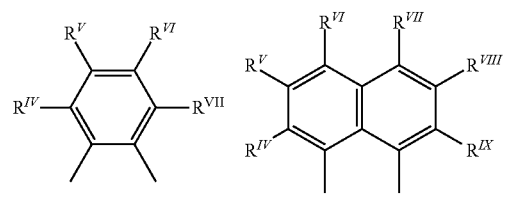

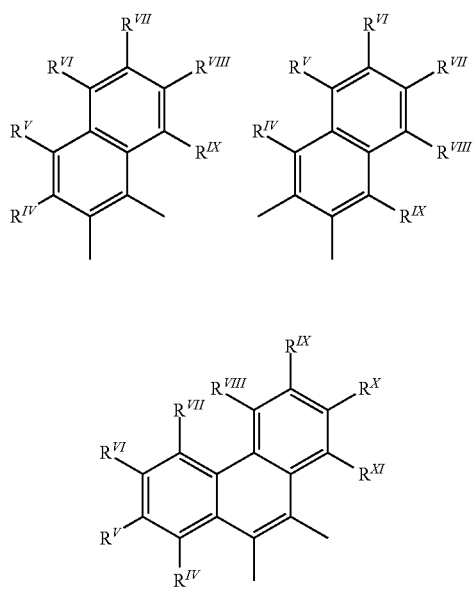

where $R^{IV}$, $R^V$, $R^{VI}$, $R^{VII}$, $R^{VIII}$, $R^{IX}$, $R^X$ and $R^{XI}$ independently are hydrogen, alkyl, alkoxy, cycloalkyl, cycloalkoxy, heterocycloalkyl, heterocycloalkoxy, aryl, aryloxy, hetaryl, hetaryloxy, halogen, hydroxy, mercapto, COOH, carboxylate, $SO_3H$, sulfonate, $NE^1E^2$, alkylene-$NE^1E^3$, nitro, alkoxycarbonyl, acyl or cyano, where $E^1$ and $E^2$ are independently hydrogen, alkyl, cycloalkyl, heterocycloalkyl, aryl or hetaryl.

Some especially preferred compounds of the formula I are as follows:

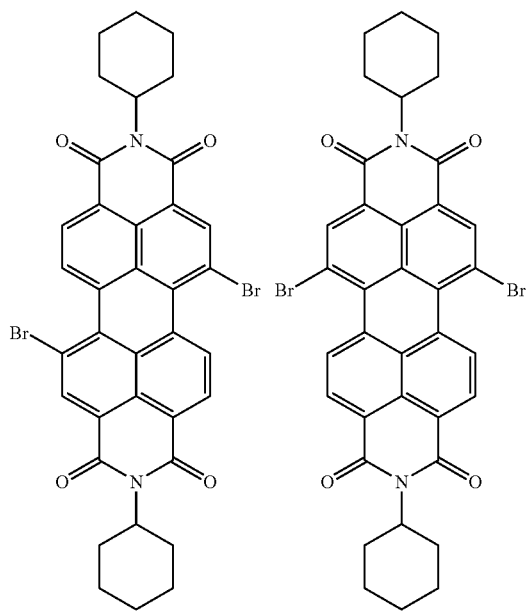

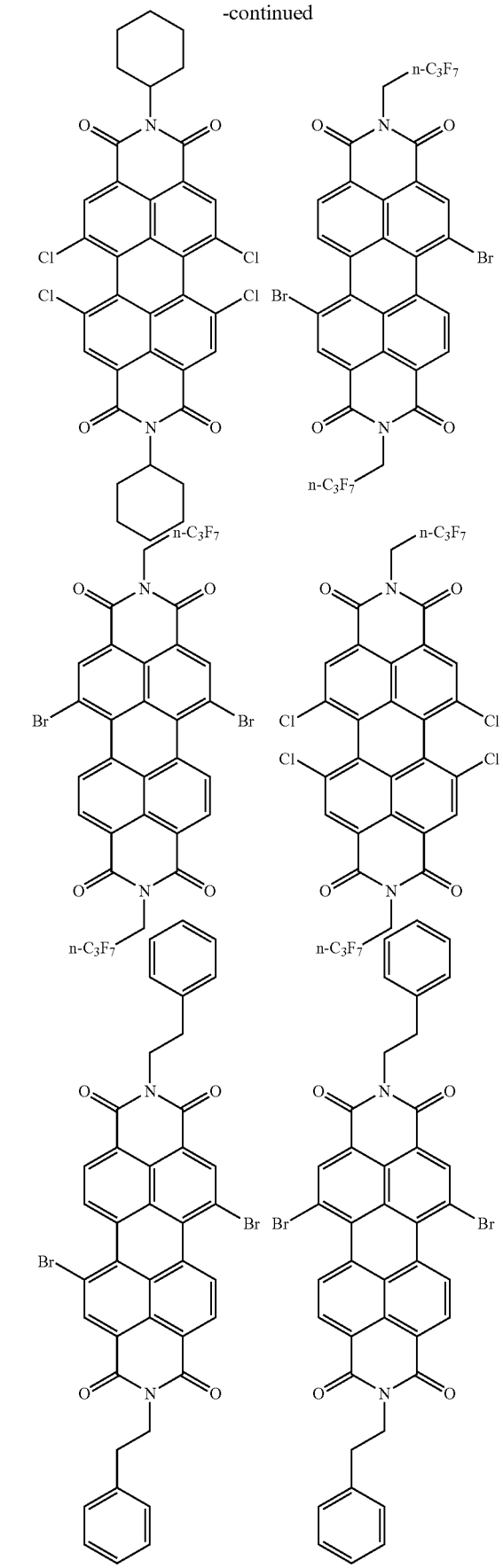

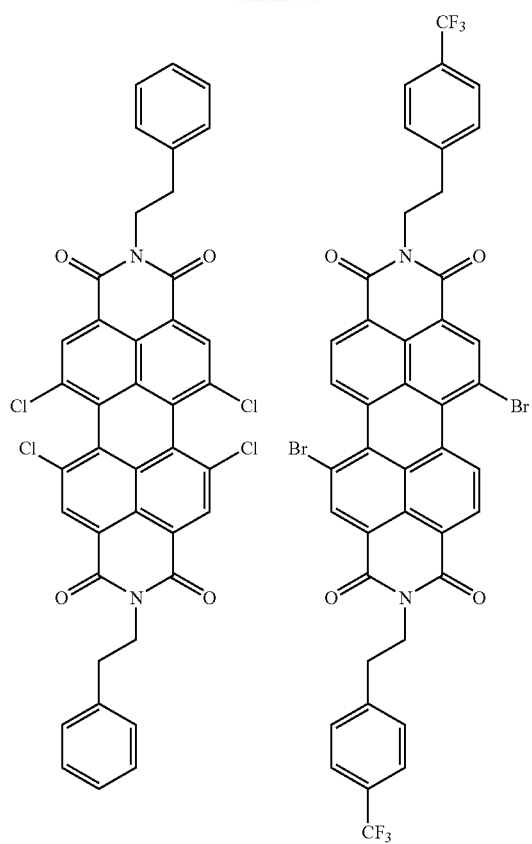
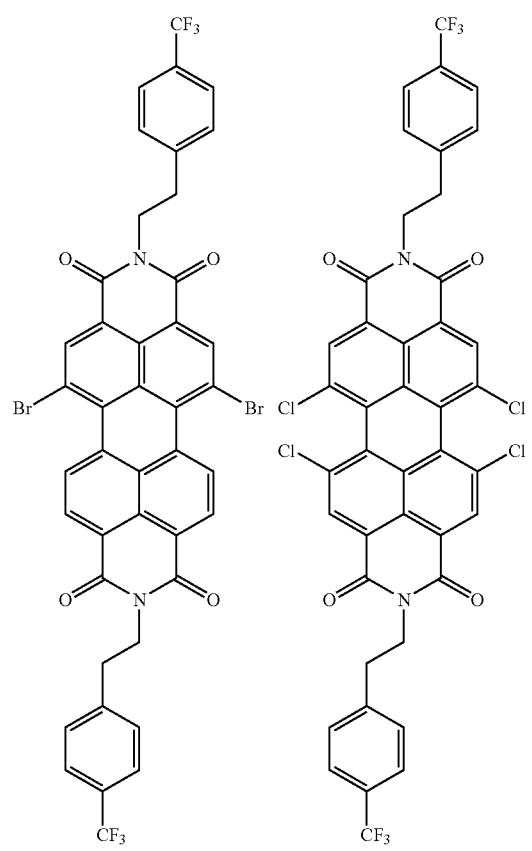
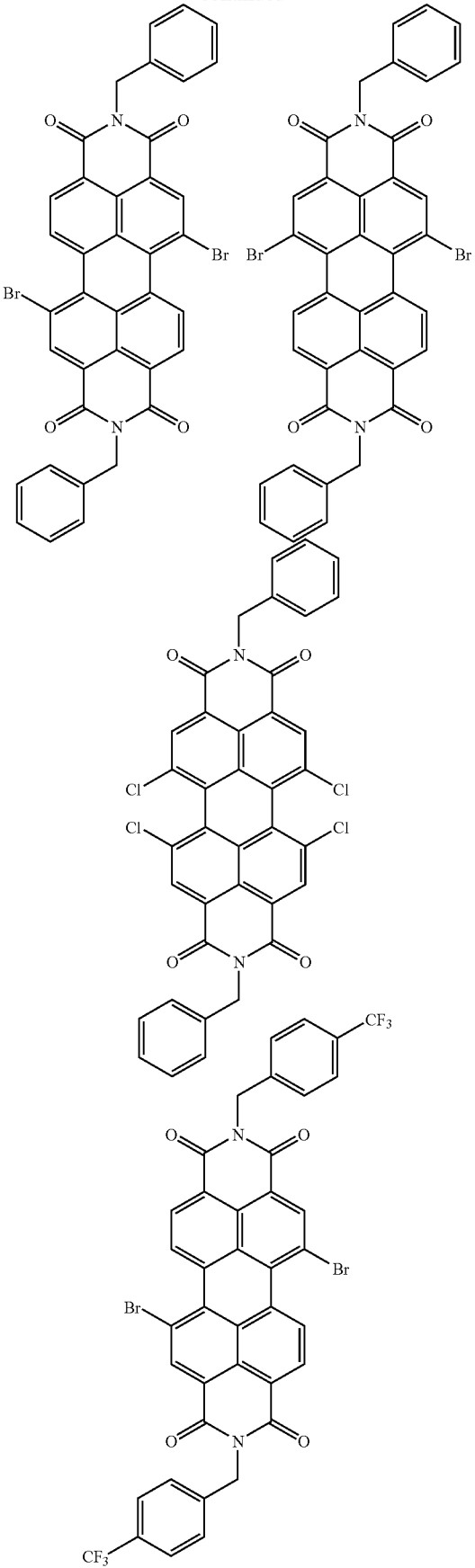

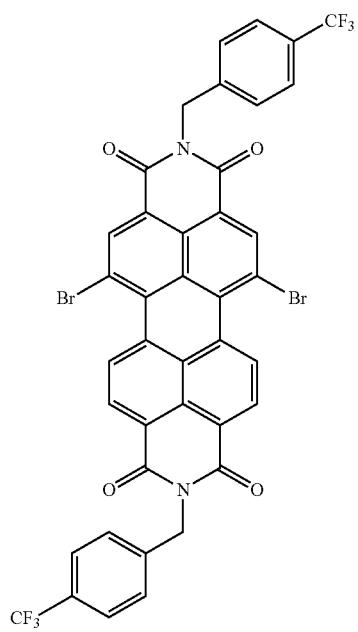
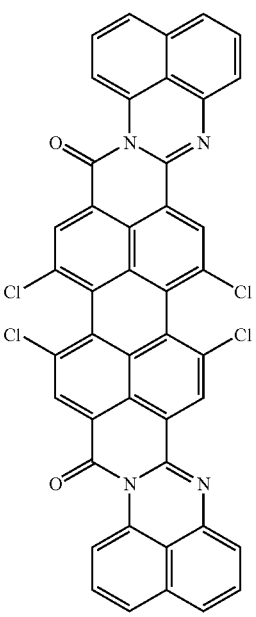
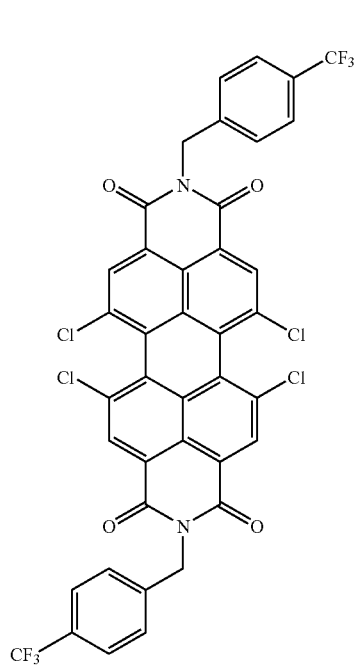
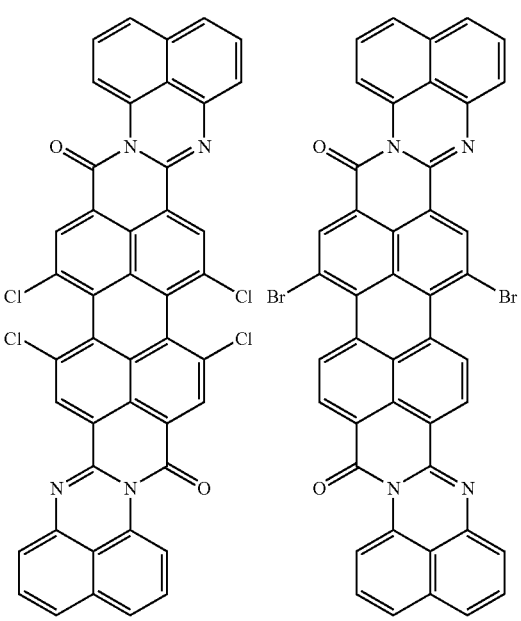

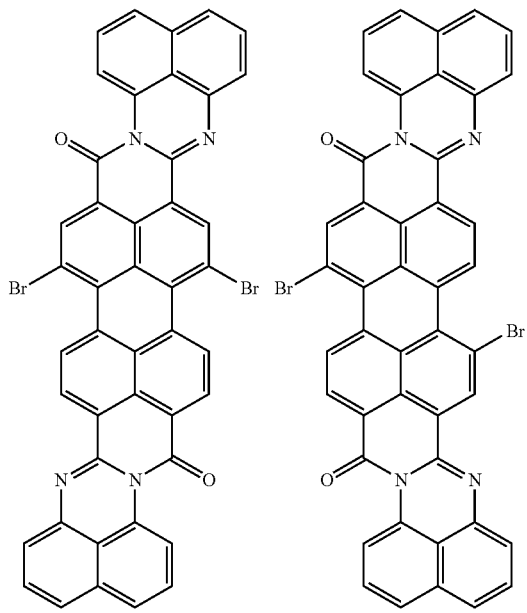
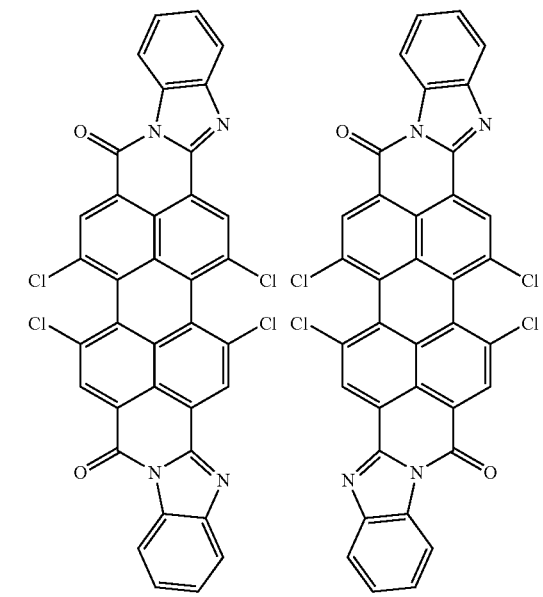
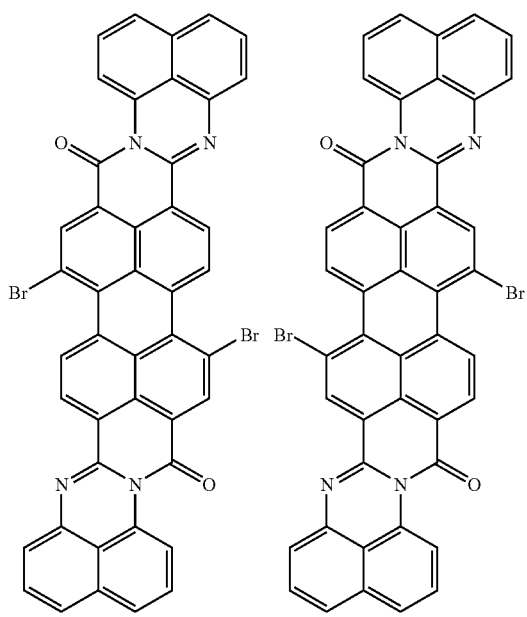
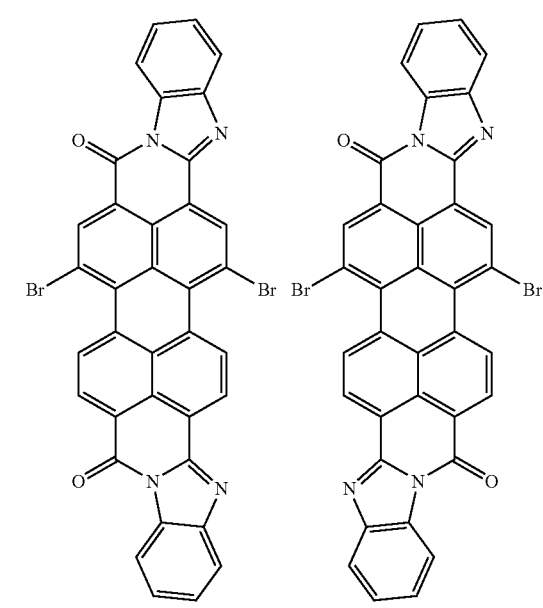

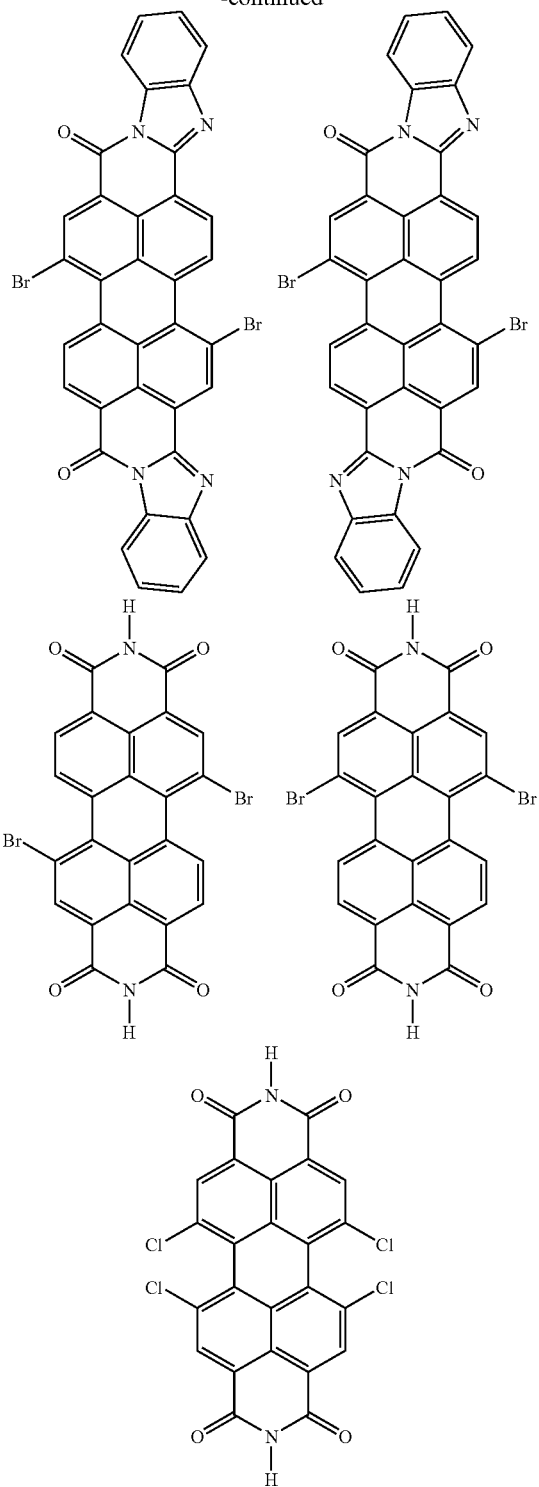

Step a)

Step a) of the method for producing an OFET comprises providing a substrate with at least one preformed transistor site located on the substrate. (It will be understood that when an element such as a layer, region or substrate is referred to as being "on" another element, it can be directly on the other element or intervening elements may be present.) In a special embodiment the substrate comprises a pattern of organic field-effect transistors, each transistor comprising:

an organic semiconductor (S) located on the substrate;
a gate structure positioned to control the conductivity of a channel portion of the crystallite; and
conductive source and drain electrodes located at opposite ends of the channel portion.

In a further special embodiment a substrate comprises a pattern of organic field-effect transistors, each transistor comprising at least one organic semiconducting compound (S) of the formula I located on the substrate forms an or is part of an integrated circuit.

Any material suitable for the production of semiconductor devices can be used as the substrate. Suitable substrates include, for example, metals (preferably metals of groups 8, 9, 10 or 11 of the periodic table, e.g. Au, Ag, Cu), oxidic materials (like glass, quartz, ceramics, $SiO_2$), semiconductors (e.g. doped Si, doped Ge), metal alloys (e.g. on the basis of Au, Ag, Cu, etc.), semiconductor alloys, polymers (e.g. polyvinylchloride, polyolefines, like polyethylene and polypropylene, polyesters, fluoropolymers, polyamides, polyurethanes, polyalkyl(meth)acrylates, polystyrene and mixtures and composites thereof, inorganic solids (e.g. ammonium chloride), and combinations thereof. The substrate can be a flexible or inflexible solid substrate with a curved or planar geometry, depending on the requirements of the desired application.

A typical substrate for semiconductor devices comprises a matrix (e.g. quartz or polymer matrix) and, optionally, a dielectric top layer (e.g. $SiO_2$). The substrate also generally includes electrodes, such as the drain and source electrodes of the OFETs, which are usually located on the substrate (e.g. deposited on the nonconductive surface of the dielectric top layer). The substrate also includes conductive gate electrodes of the OFETs that are typically located below the dielectric top layer (i.e., the gate dielectric). According to a special embodiment, the drain and source electrodes are deposited partially on the organic semiconductor rather than only on the substrate. Of course, the substrate can contain further components that are usually employed in semiconductor devices or ICs, such as insulators, resistive structures, capacitive structures, metal tracks, etc.

Step b)

The application of the n-type semiconducting compounds (S) can be carried out by known methods using lithographic techniques. Suitable are offset printing, flexo printing, etching, inkjet printing, electrophotography, physical vapor transport/deposition (PVT/PVD), chemical vapor deposition, laser transfer, dropcasting, etc.

A special embodiment for the application of the organic semiconducting compound to specific areas of the substrate makes use of a driving force that causes atoms to assemble in the desired fashion (self-assembling technique). Different methods for the self-assembly of micro-objects onto substrates are known. A first suitable technique is the fluidic self-assembly, wherein the semiconductor compounds (S) are shaped (e.g. in form of crystals) to match receptor sites or "holes" that have been etched into the substrate. The compounds (S), which are suspended in a carrier liquid that is dispensed over the substrate, fall towards the receptor sites and, with the assistance of fluid flow and/or acoustic vibration, self-orient into the holes by gravity and/or capillary force. A further suitable self-assembly technique makes use of patterned surfaces. To obtain chemical modifications the surface of the substrate can be patterned into binding and/or non-binding regions (e.g. hydrophobic/hydrophilic regions), e.g. using microcontact printing. A further suitable self-assembly technique makes use of patterned charges. According to this method, the surface of the substrate is patterned into regions with positive and/or negative charges. Organic semiconducting compounds (S) can be patterned into selected regions through electrostatic interactions. A further suitable self-assembly technique makes use of patterned topography. According to this method, a dispersion of organic semiconducting compounds is dewetted on a substrate that has been patterned with an array of templates (such as cylindrical holes). When the dispersion is allowed to dewet slowly, the capillary force leads to an assembly of the semiconductor particles in the templates. A further suitable self-assembly technique makes use of the patterning of objects through applied electric or magnetic fields. The electrical or magnetic contacts of the substrates are prefabricated. By adding an external electric or magnetic field, the organic semiconducting compounds (S) can be aligned or placed in certain regions on the substrates.

A preferred embodiment of step b) of the method according to the invention comprises:

depositing on areas of the surface of the substrate where a gate structure, a source electrode and a drain electrode are located at least one compound (C1) capable of binding to the surface of the substrate and of binding at least one organic semiconducting compound (S) of the formula I, and applying at least one organic semiconducting compound (S) to the surface of the substrate to enable at least a portion of the applied compound to bind to the areas of the surface of the substrate modified with (C1).

The free surface areas of the substrate obtained after deposition of (C1) can be left unmodified or be coated, e.g. with at least one compound (C2) capable of binding to the surface of the substrate and to prevent the binding of at least one organic semiconducting compound (S) of the formula I.

A further preferred embodiment of step b) of the method according to the invention comprises:

depositing on areas of the surface of the substrate where no gate structure, a source electrode and a drain electrode are located at least one compound (C2) capable of binding to the surface of the substrate and preventing the binding of at least one organic semiconducting compound (S) of the formula I, and applying at least one organic semiconducting compound (S) to the surface of the substrate to enable at least a portion of the applied compound to bind to the areas of the surface of the substrate not modified with (C2).

The free surface areas of the substrate obtained after deposition of (C2) can be left unmodified or be coated, e.g. with at least one compound (C1) capable of binding to the surface of the substrate and of binding at least one organic semiconducting compound (S) of the formula I.

For the purpose of the present application, the term "binding" is understood in a broad sense. This covers every kind of binding interaction between a compound (C1) and/or a compound (C2) and the surface of the substrate and every kind of binding interaction between a compound (C1) and an organic semiconducting compound (S), respectively. The types of binding interaction include the formation of chemical bonds (covalent bonds), ionic bonds, coordinative interactions, Van der Waals interactions (e.g. dipole dipole interactions), etc. and combinations thereof. In one preferred embodiment, the binding interactions between the compound (C1) and the organic semiconducting compound (S) is a non-covalent interaction.

Suitable compounds (C2) are compounds with a lower affinity to the organic semiconducting compound (S) than the untreated substrate or, if present, (C1). If a substrate is only coated with at least one compound (C2), it is critical that the strength of the binding interaction of (C2) and the substrate with the organic semiconducting compound (S) differs to a sufficient degree so that the organic semiconducting compound (S) is essentially deposited on substrate areas not patterned with (C2). If a substrate is coated with at least one compound (C1) and at least one compound (C2), it is critical that the strength of the binding interaction of (C1) and (C2) with the organic semiconducting compound (S) differs to a sufficient degree so that the organic semiconducting compound (S) is essentially deposited on substrate areas patterned with (C1). In a preferred embodiment the interaction between (C2) and the organic semiconducting compound (S) is a repulsive interaction. For the purpose of the present application, the term "repulsive interaction" is understood in a broad sense and covers every kind of interaction that prevents deposition of the crystalline compound on areas of the substrate patterned with compound (C2).

In a first preferred embodiment, the compound (C1) is bound to the surface of the substrate and/or to the organic semiconducting compound (S) of the formula I via covalent interactions. According to this embodiment, the compound (C1) comprises at least one functional group, capable of reaction with a complementary functional group of the substrate and/or the organic semiconducting compound (S).

In a second preferred embodiment the compound (C1) is bound to the surface of the substrate and/or to the organic semiconducting compound (S) of the formula I via ionic interactions. According to this embodiment, the compound (C1) comprises at least one functional group capable of ionic interaction with the surface of the substrate and/or a compound (S).

In a third preferred embodiment the compound (C1) is bound to the surface of the substrate and/or to the organic semiconducting compound (S) via dipole interactions, e.g. Van der Waals forces.

The interaction between (C1) and the substrate and/or between (C1) and the organic semiconducting compound (S) of the formula I is preferably an attractive hydrophilic-hydrophilic interaction or attractive hydrophobic-hydrophobic interaction. Hydrophilic-hydrophilic interaction and hydrophobic-hydrophobic interaction can comprise, among other things, the formation of ion pairs or hydrogen bonds and may involve further van der Waals forces. Hydrophilicity or hydrophobicity is determined by affinity to water. Predominantly hydrophilic compounds or material surfaces have a high level of interaction with water and generally with other hydrophilic compounds or material surfaces, whereas predominantly hydrophobic compounds or materials are not wetted or only slightly wetted by water and aqueous liquids. A suitable measure for assessing the hydrophilic/hydrophobic properties of the surface of a substrate is the measurement of the contact angle of water on the respective surface. According to the general definition, a "hydrophobic surface" is a surface on which the contact angle of water is >90°. A "hydrophilic surface" is a surface on which the contact angle with water is <90°. Compounds or material surfaces modified with hydrophilic groups have a smaller contact angle than the unmodified compound or materials. Compounds or material surfaces modified with hydrophobic groups have a larger contact angle than the unmodified compounds or materials.

Suitable hydrophilic groups for the compounds (C1) (as well as (C2) and/or (S)) are those selected from ionogenic, ionic, and non-ionic hydrophilic groups. Ionogenic or ionic groups are preferably carboxylic acid groups, sulfonic acid groups, nitrogen-containing groups (amines), carboxylate groups, sulfonate groups, and/or quaternized or protonated nitrogen-containing groups. Suitable non-ionic hydrophilic groups are e.g. polyalkylene oxide groups. Suitable hydrophobic groups for the compounds (C1) (as well as (C2) and/or (S)) are those selected from the aforementioned hydrocarbon groups. These are preferably alkyl, alkenyl, cycloalkyl, or aryl radicals, which can be optionally substituted, e.g. by 1, 2, 3, 4, 5 or more than 5 fluorine atoms.

In order to modify the surface of the substrate with a plethora of functional groups it can be activated with acids or bases. Further, the surface of the substrate can be activated by oxidation, irradiation with electron beams or by plasma treatment. Further, substances comprising functional groups can be applied to the surface of the substrate via chemical vapor deposition (CVD).

Suitable functional groups for interaction with the substrate include:
  silanes, phosphonic acids, carboxylic acids, and hydroxamic acids:
    Suitable compounds (C1) comprising a silane group are alkyltrichlorosilanes, such as n-(octadecyl)trichlorosilane (OTS); compounds with trialkoxysilane groups, e.g. trialkoxyaminoalkylsilanes like triethoxyaminopropylsilane and N[(3-triethoxysilyl)-propyl]-ethylen-diamine; trialkoxyalkyl-3-glycidylethersilanes such as triethoxypropyl-3-glycidylethersilane; trialkoxyallylsilanes such as allyltrimethoxysilane; trialkoxy(isocyanatoalkyl)silanes; trialkoxysilyl(meth)acryloxyalkanes and trialkoxysilyl(meth)acrylamidoalkanes, such as 1-triethoxysilyl-3-acryloxypropan.
    (These groups are preferably employed to bind to metal oxide surfaces such as silicon dioxide, aluminium oxide, indium zinc oxide, indium tin oxide and nickel oxide.),
  amines, phosphines and sulfur containing functional groups, especially thiols:
    (These groups are preferably employed to bind to metal substrates such as gold, silver, palladium, platinum and copper and to semiconductor surfaces such as silicon and gallium arsenide.)

In a preferred embodiment, the compound (C1) is selected from $C_8$-$C_{30}$-alkylthiols and is in particular hexadecane thiol. In a further preferred embodiment the compound (C1) is selected from mercaptocarboxylic acids, mercaptosulfonic acids and the alkali metal or ammonium salts thereof. Examples of these compounds are mercaptoacetic acid, 3-mercaptopropionic acid, mercaptosuccinic acid, 3-mercapto-1-propanesulfonic acid and the alkali metal or ammonium salts thereof, e.g. the sodium or potassium salts. In a further preferred embodiment the compound (C1) is selected from alkyltrichlorosilanes, and is in particular n-(octadecyl)trichlorosilane (OTS).

Additionally to or as an alternative to deposition of said compound (C1) on the substrate, the substrate can be contacted with at least one compound (C2) capable of binding to the surface of the substrate as well as of interaction with the organic semiconducting compound (S) to prevent deposition of (S) on areas of the substrate not patterned with compound (C1). According to a suitable embodiment, the compounds (C2) are selected from compounds with a repulsive hydrophilic-hydrophobic interaction with (S).

According to a preferred embodiment, the organic semiconductor compound (S) of the formula I is employed in the form of crystals, more preferably in the form of crystallites. For the purpose of the invention, the term "crystallite" refers to small single crystals with maximum dimensions of 5 millimeters. Exemplary crystallites have maximum dimensions of 1 mm or less and preferably have smaller dimensions (frequently less than 500 µm, in particular less than 200 µm, for example in the range of 0.01 to 150 µm, preferably in the range of 0.05 to 100 µm), so that such crystallites can form fine patterns on the substrate. Here, an individual crystallite has a single crystalline domain, but the domains may include one or more cracks, provided that the cracks do not separate the crystallite into more than one crystalline domain. The stated particle sizes and the crystallographic properties of the crystallites can be determined by direct X-ray analysis. During the preparation of semiconductor devices preferably appropriate conditions e.g. treatment of the substrate, temperature, evaporation rate etc. are employed to obtain films having high crystallinity and large grains.

The particles of the semiconductor compound (S) may be of regular or irregular shape. For example, the particles can be present in spherical or virtually spherical form or in the form of needles.

Preferably the organic semiconductor (S) is employed in the form of particles with a length/width ratio (L/W) of at least 1.05, more preferably of at least 1.5, especially of at least 3.

In an organic field-effect transistor (OFET), a channel made of a single organic semiconductor crystal will typically have greater mobility than a channel made of a polycrystalline organic semiconductor. The high mobility results from the fact that the single crystal channel does not have grain boundaries. Grain boundaries lower the conductivity and mobility of OFET channels made of polycrystalline organic semiconductor films.

Organic semiconductor crystal in general and especially crystallites can be obtained by sublimation of the compounds of the formula I. A preferred method makes use of physical vapor transport/deposition (PVT/PVD) as defined in more detail in the following. Suitable methods are described by R. A. Laudise et al in "Physical vapor growth of organic semiconductors" Journal of Crystal Growth 187 (1998) pages 449-454 and in "Physical vapor growth of centimeter-sized crystals of α-hexathiophene" Journal of Crystal Growth 182 (1997) pages 416-427. Both of these articles by Laudise et al are incorporated herein in their entirety by reference. The methods described by Laudise et al include passing an inert gas over an organic semiconductor substrate that is maintained at a temperature high enough that the organic semiconductor evaporates. The methods described by Laudise et al also include cooling down the gas saturated with organic semiconductor to cause an organic semiconductor crystallite to condense spontaneously.

A further object of the invention is the use of compounds of the formula I as defined before as n-type semiconductors. They are especially advantageous as n-type semiconductors for organic field-effect transistors, organic solar cells and organic light emitting diodes (OLEDs).

A further object of the invention is to provide a process for preparing a compound of the formula

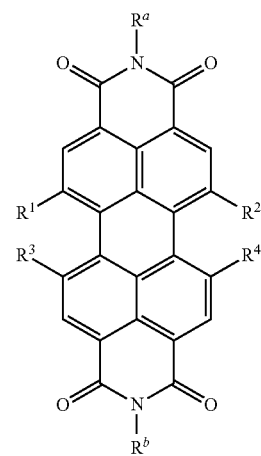

where
  $R^1$, $R^2$, $R^3$ and $R^4$ are independently hydrogen, chlorine or bromine, with the proviso that at least one of these radicals is not hydrogen,
  $R^a$ and $R^b$ are independently hydrogen or unsubstituted or substituted alkyl, alkenyl, alkadienyl, alkynyl, cycloalkyl, bicycloalkyl, cycloalkenyl, heterocycloalkyl, aryl oder hetaryl, wherein a rylenedianhydride of the formula Ia,

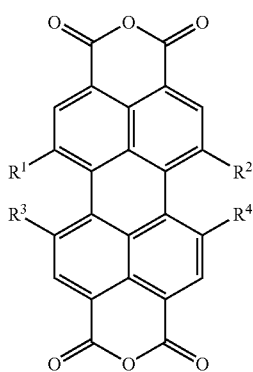

is reacted with an amine of the formula $R^a$—$NH_2$ and, optionally, a further amine of the formula $R^b$—$NH_2$, different from amine $R^a$—$NH_2$.

A further object of the invention is to provide a process for preparing a compound of the formula

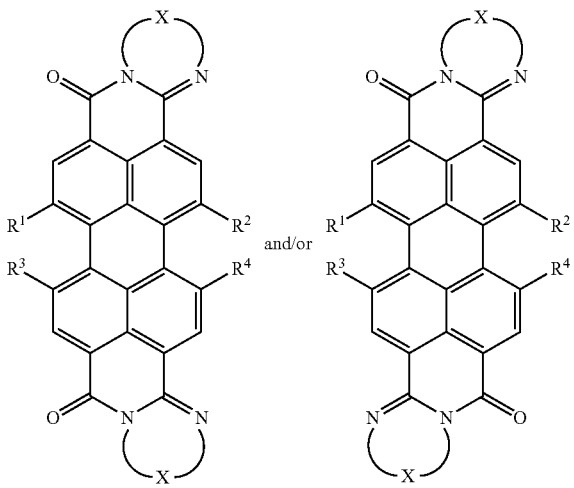

where
$R^1$, $R^2$, $R^3$ and $R^4$ are independently hydrogen, chlorine or bromine, with the proviso that at least one of these radicals is not hydrogen,
X is a bridging group having 2 to 5 atoms between the terminal bonds,
wherein a rylenedianhydride of the formula Ia,

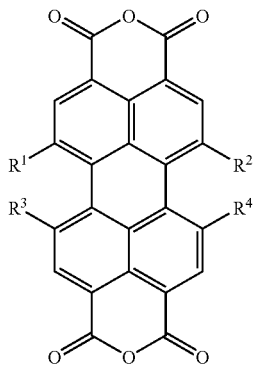

is reacted with an amine of the formula $H_2N$—X—$NH_2$.

The imidization of carboxylic anhydrides is known per se. The reaction of the dianhydride with a primary amine is preferably carried out in an aromatic solvent, such as toluene, xylene, mesitylene, phenol or a polar aprotic solvent. Suitable polar aprotic solvents are N-heterocycles, like pyridine, pyrimidine, quinoline, isoquinoline, quinaldine, N-methylpiperidine, N-methylpiperidone and N-methylpyrrolidone. Suitable solvents are also carboxylic acids, e.g. acetic acid, propionic acid, butyric acid and mixtures of carboxylic acids and carboxamides.

The reaction with an aromatic diamine of the formula $H_2N$—X—$NH_2$ is preferably carried out in a high-boiling organic solvent, like nitrobenzene, dichlorobenzene, trichlorobenzene, α-chloronaphthalene, quinoline, tetraline, n-methylpyrrolidone, N,N-dimethylformamide, ethyleneglycol, glacial acetic acid and cyclic urea derivatives. Especially preferred is phenol.

Suitable catalysts for the imidization are organic and inorganic acids, e.g. formic acid, acetic acid, propionic acid, phosphorous acid, etc. Further suitable catalysts are organic and inorganic salts of transition metals, such as zinc, iron, copper and magnesium, e.g. zinc acetate, zinc propionate, zinc oxide, iron(II)-acetate, iron(III)-chloride, iron(II)-sulfate, copper(II)-acetate, copper(II)-oxide and magnesium-acetate. The use of a catalyst is preferred for the reaction of aromatic amines and can also be advantageous for the reaction of cycloaliphatic amines. If phenol is used as the solvent, a preferred catalyst is piperazine.

The catalyst is preferably employed in an amount of from 5 to 80 weight-%, especially 10 to 75 weight-%, with regard to total weight of the compound to be imidized.

The molar ratio of amine to dianhydride is preferably about 2:1 to 4:1, more preferably 2.2:1 to 3:1.

The reaction temperature is preferably from ambient temperature up to 200° C., more preferably 40 to 160° C. Aliphatic and cycloaliphatic amines are preferably reacted at a temperature of from 60° C. to 100° C. Aromatic amines are preferably reacted at a temperature of from 120 to 160° C.

The reaction can be carried out under inert atmosphere, e.g. under nitrogen atmosphere.

The reaction can be carried out under ambient pressure or higher pressure. A suitable pressure range is from about 0.8 to 10 bar. Volatile amines (boiling point ≦180° C.) are preferably reacted under superatmospheric pressure.

The water formed in the reaction can be separated off by known measures, e.g. by distillation or codistillation e.g. with toluene. If a diamine is employed in the condensation reaction, it is usually necessary to separate off the water, e.g. by distillation.

Compounds of the formula I with sufficient solubility in organic solvents can be purified by recrystallization or by column chromatography. Suitable solvents for column chromatography are e.g. halogenated hydrocarbons, like methylene chloride. Compounds of the formula I with low solubility in organic solvents can be recrystallized from sulfuric acid.

In an alternative embodiment, purification of the compounds of formula I can be carried out by sublimation. Preferred is a fractionated sublimation. For fractionated sublimation, the sublimation and/or the deposition of the compound is effected by using a temperature gradient. Preferably the compound of the formula I sublimes upon heating in flowing carrier gas. The carrier gas flows into a separation chamber. A suitable separation chamber comprises different separation zones operated at different temperatures. Preferably a so-called three-zone furnace is employed. A further suitable method and apparatus for fractionated sublimation is described in U.S. Pat. No. 4,036,594.

In a further embodiment an organic semiconducting compound of the formula I is subjected to purification and/or crystallization by physical vapor transport. Physical vapor transport (PVT) and physical vapor deposition (PVD) are vaporisation/coating techniques involving transfer of material on an atomic level. PVD processes are carried out under vacuum conditions and involve the following steps:
Evaporation
Transportation
Deposition The process is similar to chemical vapour deposition (CVD) except that CVD is a chemical process wherein the substrate is exposed to one or more volatile precursors, which react and/or decompose on the substrate surface to produce the desired deposit. It was surprisingly found that compounds of the formula I can be subjected to a CVT essentially without decomposition and/or the formation of undesired by-products. The deposited material is obtained in high purity and in the form of crystals with excellent purity, homogeneity and size for use as n-type semiconductors. One aspect is a physical vapor transport crystal growth wherein a solid source material is heated above its vaporization temperature and the vapor allowed to crystallize by cooling below the crystallization temperature of the material. The obtained crystals can be collected and afterwards applied to specific areas of a substrate by known techniques, as mentioned above. A further aspect is a method for patterning the surface of a substrate with at least one organic semiconducting compound of the formula I by CVD. According to this aspect, a substrate with a surface that has a preselected pattern of deposition sites located thereupon is preferably used. The deposition sites can be formed from any material that allows selective deposition on the surface of the substrate. Suitable compounds are the aforementioned compounds C1, which are capable of binding to the surface of the substrate and of binding at least one compound of the formula I.

The invention will now be described in more detail on the basis of the accompanying figure and the following examples.

EXAMPLES

Examples

General procedure for purification of organic semiconducting compounds by physical vapor transport:

In the apparatus according to FIG. 1, single crystals of organic semiconducting compounds were grown by horizontal physical vapor transport in a carrier gas stream of high purity argon. The temperature gradient was about 5° C./cm. The starting material was heated to 510° C. The obtained single crystals were used for the manufacturing of OFETs.

Example 1

1,6,7,12-Tetrachloro-N,N'-dicyclohexyl-perylene-3,4:9,10-tetracarboxylic diimide.2 N-methylpyrrolidone

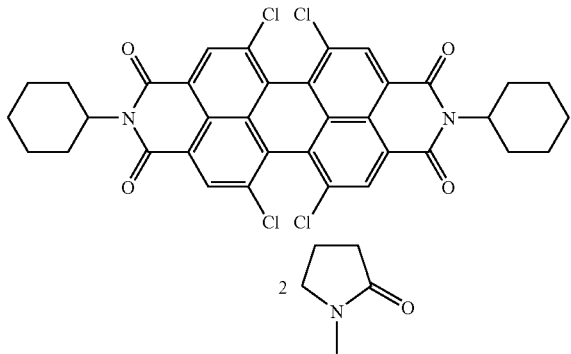

A mixture of 40.0 g (75.6 mmol) of 1,6,7,12-tetrachloroperylen-3,4:9,10-tetracarboxylic dianhydride, 22.2 g (224 mmol) of cyclohexylamine and 600 ml of n-methylpyrrolidone and 28 g of acedic acid was heated to 90° C. and kept at this temperature for 11 hours. The reaction mixture was cooled to room temperature. The precipitate was collected by filtration and washed with methanol and dried at 55° C., 66.1 g of a red product was obtained. The yield fits to a quantitative yield of a solvate with two NMP molecules.

Example 2

1,6,7,12Tetrachloro-N,N'-benzyl-perylene-3,4:9,10-tetracarboxylic diimide

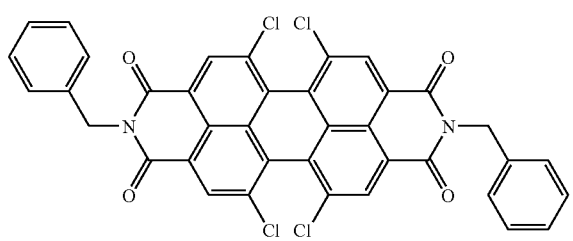

2.65 g (5 mmol) of 1,6,7,12-tetrachloroperylen-3,4:9,10-tetracarboxylic dianhydride, 1.1 g (10 mmol) of benzylamine and 25 ml of xylene were heated to 75° C. for 2.5 hours. Another portion of 0.5 g (5 mmol) of benzylamine was added and the mixture stirred at 75° C. for 5 hours. The reaction mixture was cooled to room temperature, filtered and washed with ethanol and dried. 4.5 g were obtained, which were subjected to column chromatography using toluene ethyl acetate 30:1. 2.6 g (73%) of a red solid were obtained.

$R_f(CH_2Cl_2)=0.53$

Example 3

1,6,7,12-Tetrachloro-N,N'-phenethyl-perylene-3,4:9,10-tetracarboxylic diimide

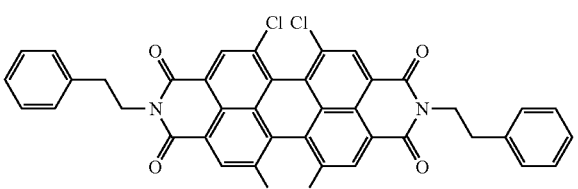

The reaction was carried out exactly as described above. Equimolar amounts of phenethylamine were used instead of benzylamine. The crude product was purified by column chromatography.1.8 g (49%) of a red solid were obtained.

$R_f(Toluene:CH_2Cl_2\ 1:1)=0.2$

Example 4

1,6,7,12-Tetrachloroperylenperimidin

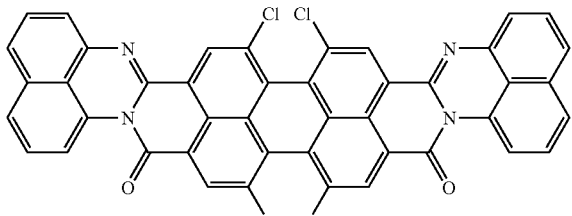
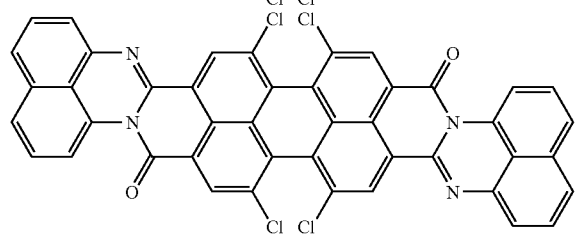

A mixture of 5.3 g (10 mmol) of 1,6,7,12-tetrachloroperylen-3,4:9,10-tetracarboxylic dianhydride and 3.6 g (22 mmol) of 1,8-diaminonaphthalene and 1.76 g (22 mmol) of pyrazine was heated to 170° C. Water was distilled off in order to reach a temperature of 170° C. The mixture was stirred at this temperature for 24 hours. The reaction mixture was cooled to 70° C., methanol was added and the mixture was filtered. In order to achieve a better turnover to the desired product, the procedure was repeated with the product obtained from the first reaction. The precipitate was washed with water, 500 ml of methanol, 250 ml of 10% NaOH and with hot water. 7.2 g (93%) of a black material was obtained.

Example 5

1,6,7,12-Tetrachloroperylenbisbenzimidazole

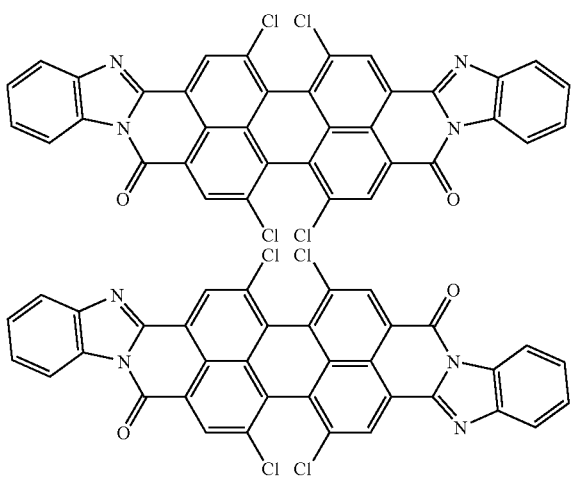

A mixture of 5.3 g (10 mmol) of 1,6,7,12-tetrachloroperylen-3,4:9,10-tetracarboxlic dianhydride, 4.75 g (44 mol) of o-diaminobenzene, 3.52 g (44 mmol) of pyrazine and 50 g of phenol was heated to 125° C. Water was distilled off and 50 ml of toluene were added. Toluene and water were distilled off. At 156° C. another portion of 100 g of phenol was added and the reaction mixture was kept at 156° C. for 24 hours. The mixture was cooled to room temperature, 100 ml of methanol were added and the product was isolated by filtration. The residue was washed with 500 ml of methanol, then with 50 ml of 10% NaOH solution and finally with hot water. After drying 6.3 g (93) of a black solid were obtained.

$R_f$ (trichloroacetic acid:toluene=1:5)=0.33; 0.50

Example 6

1,7-Dibromo-N,N'-dicyclohexyl-perylene-3,4:9,10-tetracarboxylic diimide

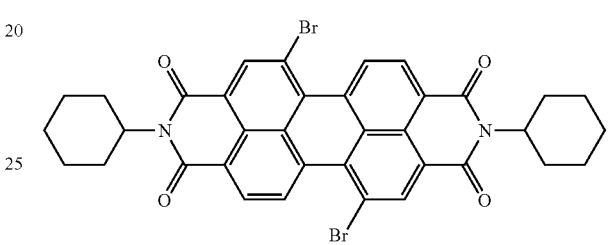

A mixture of 16.5 g (30 mmol) of 1,7-dibromoperylen-3,4;9,10-tetracarboxylic dianhydride and 9.0 g (90 mmol) of cyclohexylamine, 11 g of acetic acid and 240 ml of NMP was heated to 90° C. for 16 hours. After cooling the reaction mixture to room temperature, the product was precipitated by pouring the reaction mixture into 1000 ml of water. The residue was filtered, washed with water and dried in vacuum. The crude product was purified by column chromatography using toluene as eluent. 9.5 g (44%) of a red solid were obtained. Due to the purification by column chromatography only the 1,7 isomer was obtained and no 1,6 isomer was present in the sample.

$R_f(CH_2Cl_2)$=0.5

Example 7

1,7-Dibromo-N,N'-benzyl-perylene-3,4:9,10-tetracarboxylic diimide

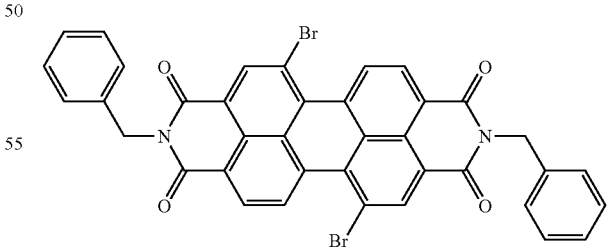

A mixture of 110 g (20 mmol) of 1,7-Dibromo-perylene-3,4:9,10-tetracarboxylic dianhydride was heated together with 4.4 g (40 mmol) of benzylamine in 100 ml of xylene to 75° C. for six hours. Then another portion of 4.4 g (40 mmol) benzylamine was added and the reaction was stirred for 6 further hours at 75° C. The reaction mixture was filtered, washed with xylene and ethanol and dried. 13.9 g of crude material were obtained. 4.0 g of this crude material were purified by heating in 80 ml of NMP to 150° C., cooling to 60° C., filtering and washing with NMP and ethanol. 3.2 g (76%) of a pure red material were obtained. Due to the purification step no 1,6 isomer was present in the product.

$R_f$(CH$_2$Cl$_2$:toluene 1:1)=0.1

Example 8

1,7-Dibromo-N,N'-phenethyl-perylene-3,4:9,10-tetracarboxylic diimide

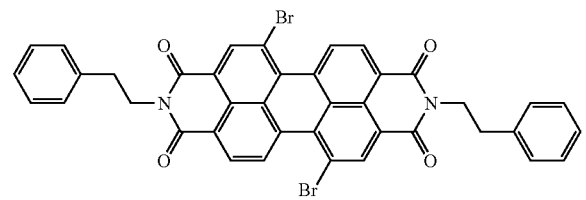

The reaction and the purification were carried out exactly as described above. 72% of a dark material was obtained. Due to the purification step no 1,6 isomer was present in the product.

$R_f$(toluene:ethyl acetate 30:1)=0.2

Example 9

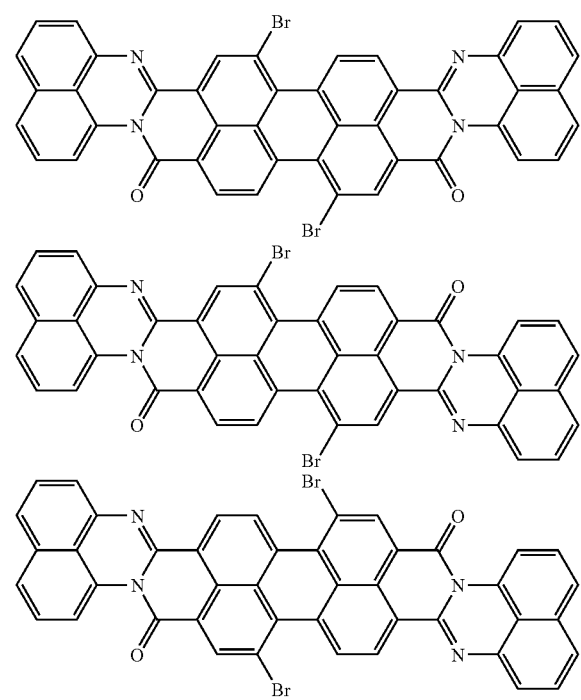

A mixture of 11.4 g (72 mmol) of 1,8-diaminonaphthalene, 2.88 g (36 mmol) of pyrazine and 100 g of phenol was heated to 120° C. Then 9.9 g (18 mmol) of 1,7-dibromo-perylene-3,4:9,10-tetracarboxylic dianhydride were added and the mixture was heated to 170° C. Water was distilled off. 60 ml of toluene were added and 50 g of phenol were added. After distilling off water and toluene the mixture was kept at 183° C. for 140 hours.

The workup will be carried out as described above for example 4 and 5.

Example 10

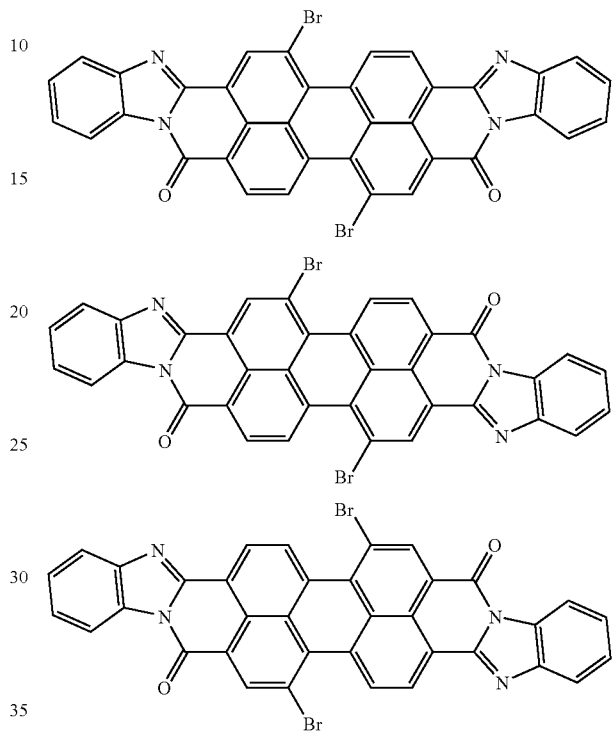

The reaction was carried out as described above for example 9. 1,2-Diaminobenzene was used instead of 1,8-diaminonaphthalene.

Example 11

Use of 1,6,7,12-Tetrachloroperylentetracarbonic acid diimide

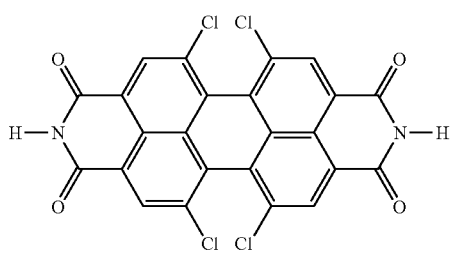

The compound was synthesized according to known procedures. 1 mm single crystals were produced by physical vapour deposition in the apparatus according to FIG. 1 by the general procedure. The obtained single crystals were employed to build an OFET on a substrate comprising a 300 nm SiO$_2$ layer as dielectric material. The obtained transistor had a W/L ratio of 7, a capacity C of 10 nF/cm$^2$ and a mobility of 0.014 cm$^2$/Vs with an on/off ratio of 58048.

Example 12

Use of 1,6,7,12-tetrachloroperylentetracarboxylic diimide

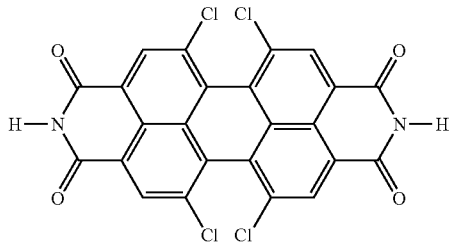

The compound was synthesized according to known procedures. The compound was purified three times with a three zone furnace:

First Furnace
T1=340° C., T2=290° C., T3=250° C. vacuum level 2.7×10$^{-6}$ torr, starting with 0.24 g yielding 0.15 g in area T2 and yielding 0.10 g in area T3

Second Furnace
T1=32020 C., T2=290° C., T3=250° C. vacuum level 3.2×10$^{-6}$ torr, starting with 0.15 g yielding 0.08 g in area T2 and yielding 0.05 g in area T3

Third Furnace
T1=300° C., T2=290° C., T3=250° C. vacuum level 2×10$^{-6}$ torr, starting with 0.08 g yielding 0.05 g in area T2

Material in T2 after the third furnace purification was evaporated onto an octadecyltrichlorosilane pretreated SiO$_2$ with a substrate temperature of 90° C. A mobility of 0.08 cm$^2$/Vs was measured with an on/off ratio of 9112.

Example 13

The purified material from example 12 was used on an OTS pretreated substrate at 125° C. A mobility of 0.11 cm$^2$/Vs and an on/off ratio of 4470000 were established.

Example 14

The purified material from example 12 was used on an OTS pretreated substrate at 150° C. A mobility of 0.10 cm$^2$/Vs and an on/off ratio of 1810000 were established.

Example 15

The purified material from example 12 was used on an OTS pretreated substrate at 200° C. A mobility of 0.11 cm$^2$/Vs and an on/off ratio of 4470000 were established.

Example 16

Use of 1,6,7,12-tetrachloroperylentetracarboxylic diimide in inverters 1,6,7,12-tetrachloroperylentetracarboxylic diimide (TC-PTCDI) and pentacene were purified by three consecutive vacuum sublimations using a three-temperature-zone furnace (Lindberg/Blue Thermo Electron Corporation) under high vacuum (less than 5×10$^6$ Torr). The starting material was placed in the first temperature zone. The three temperature zones were set to be 340° C., 270° C. and 250° C. for 1,6,7,12-tetrachloroperylentetrcarboxylic diimide and 249° C., 160° C. and 100° C. for pentacene, respectively. A highly doped n$^{++}$ silicon substrate was used as a common gate electrode. A thermally grown silicon dioxide (300 nm, capacitance $C_i$=10 nF/cm$^2$) was used as the dielectric layer. The substrates were cleaned by rinsing with acetone followed by isopropyl alcohol and then treated with octadecyl-trimethoxysilane (C$_{18}$H$_{37}$Si(OCH$_3$)$_3$, OTS). A few drops of pure OTS were loaded on top of a preheated quartz block (~100° C.) inside a vacuum desiccator. The desiccator was immediately evacuated (~25 mmHg) and the SiO$_2$/Si substrate was treated with the OTS to give a hydrophobic surface. Finally, the substrates were then baked at 110° C. for 15 min, rinsed with isopropanol and dried with a stream of air. For the production of top contact n-type transistors a TC-PTCDI layer (45 nm thickness) was deposited on top of the substrates at a pressure less than 2×10$^{-6}$ torr with a deposition rate of 1.0 Å/s using a vacuum thin-film deposition system (Angstrom Engineering, Inc., Canada). The substrates were held at about 150° C. during thin film deposition. Elevated substrate temperature was found to lead to larger grain size and thus higher charge carrier mobilities. The area for the n-type film is about 1 cm by 2 cm. The rest of the area was covered by a thin glass mask during the film deposition of the p-type semiconductor.

For the production of top contact p-type transistors, a pentacene layer (45 nm thickness) was deposited on top of the substrates at a pressure less than 2×10$^{-6}$ torr with a deposition rate of 1.0 Å/s while covering the thin films of perylene derivatives that had been already deposited. The substrates were held at 60° C. during thin film deposition. Shadow masks with various channel length (L) and width (W) were used for gold (ca. 40 nm) metal evaporation to make both p-type and n-type top-contact thin film transistors. In order to match the source/drain current from both types of transistors to achieve optimum operation conditions for the inverters, W/L of 10 (ie., W/L=2000 µm/200 µm) and 50 (ie., W/L=2500 µm/50 µm) were used for p-type and n-type transistors, respectively. To form an inverter, both the drain electrodes from each of the p-type and n-type transistors were connected using an aluminum wire with both of its ends attached to the gold electrodes with a soft metal such as Indium.

Figure 2:
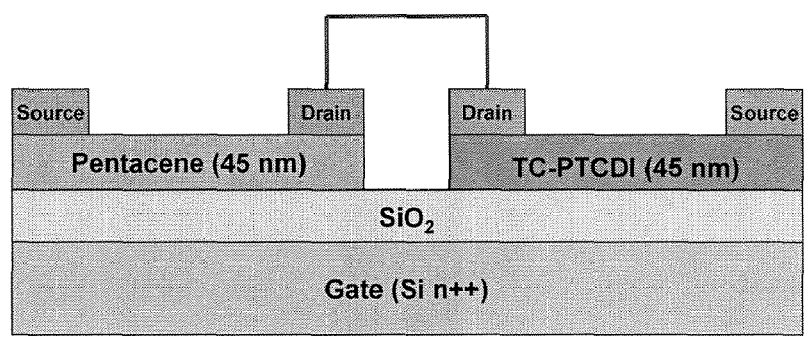
FIG. 2 shows the structure of an inverter structure comprising 1,6,7,12-tetrachloroperylentetracarboxylic diimide as n-type transistor and pentacene as p-type transistors.
Figure 2:
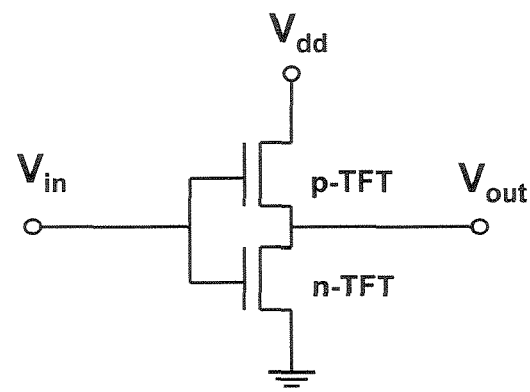
Figure 3A:
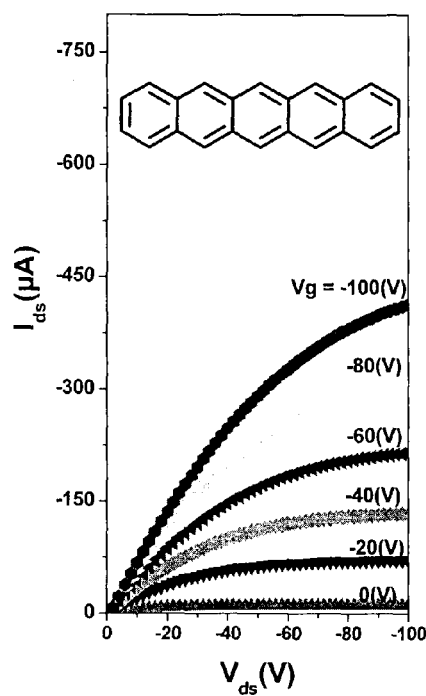
FIGS. 3(a) and 3(b) show typical current-voltage characteristics of pentacene.
Figure 3B:
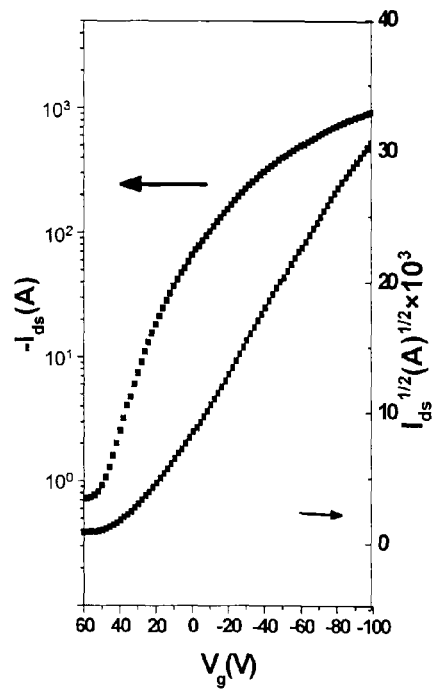
Figure 4A:
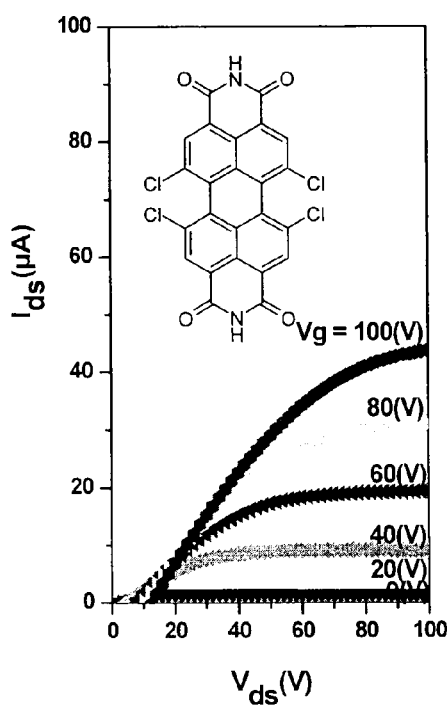
FIGS. 4(a) and 4(b) show typical current-voltage characteristics of 1, 6, 7, 12-tetrachloroperylentetracarboxylic diimide.
Figure 4B:
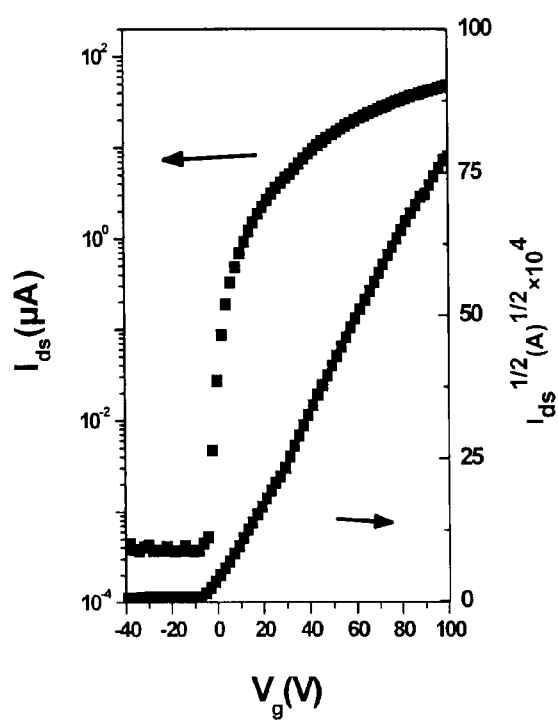
Figure 5:
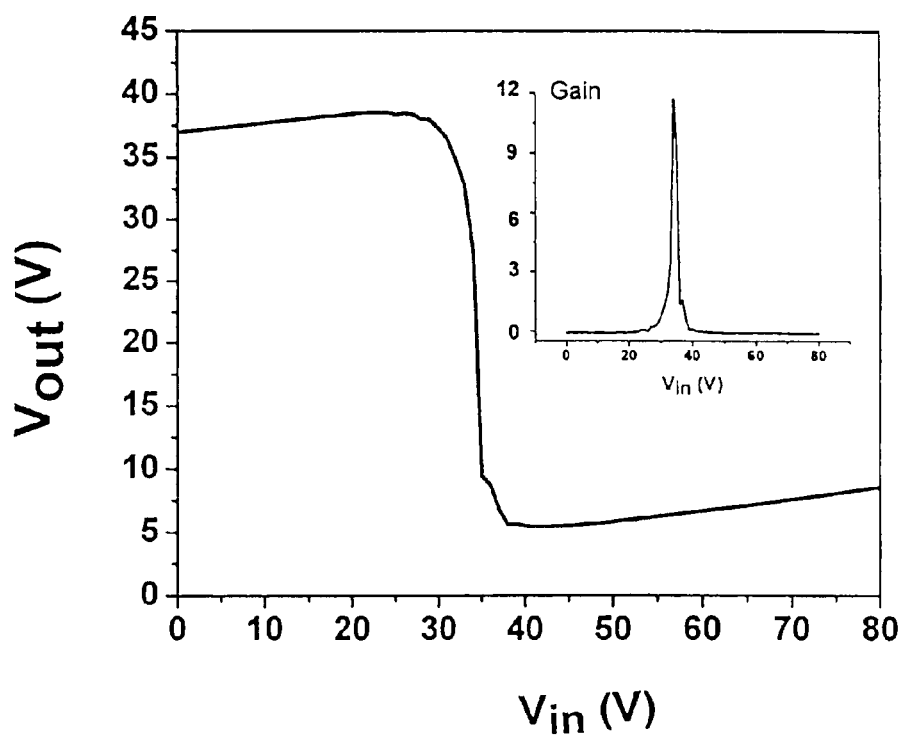
FIG. 5 shows that the highest gain for a TC-PTCDI inverter for $V_{dd}$=40V is about 12, the noise margin is 4.5V and the output voltage swing is about 33V.
Figure 6:
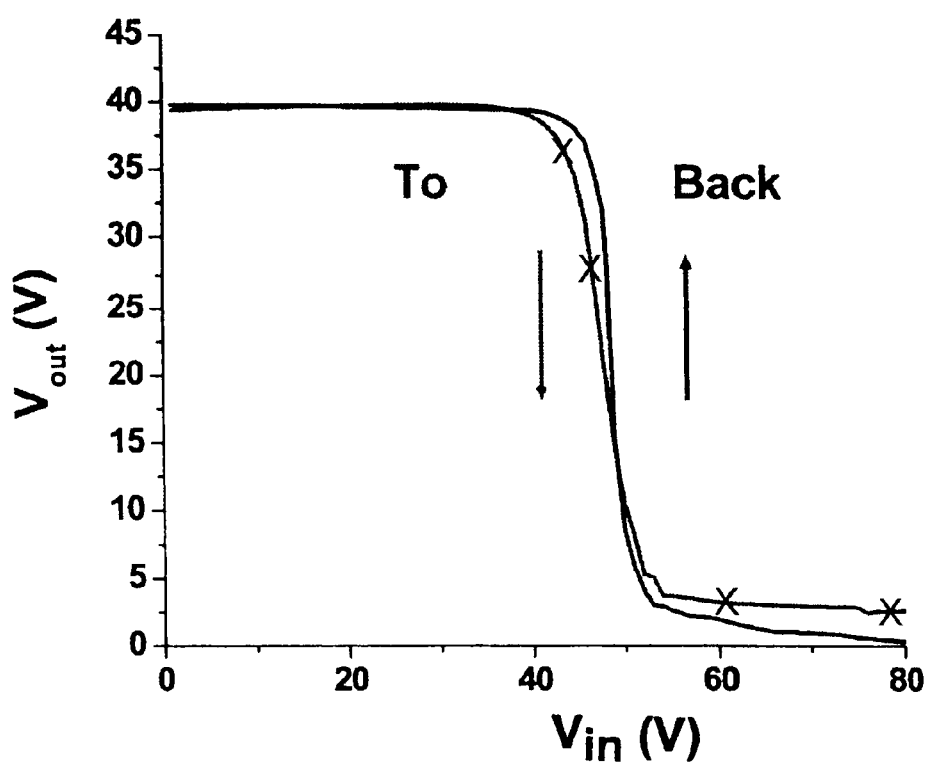
FIG. 6 shows the hysteresis for TC PTCDI.

The final inverter structure is shown in FIG. 2. OTFTs with a W/L ratio of 20 were made as references. The electrical characteristics of OTFT devices and the corresponding inverters were measured using a Keithley 4200-SCS semiconductor parameter analyzer in ambient lab environment. Key device parameters for transistors such as charge carrier mobilities were extracted from the drain-source current ($I_d$)-gate voltage ($V_g$) characteristics. Parameters for the inverter such as gain, noise margin and output voltage swing were extracted from the transfer curves of output voltage ($V_{out}$) vs. input voltage ($V_{in}$). Typical current-voltage characteristics of pentacene and TC-PTCDI are shown in FIGS. 3(a) and 3(b). The extracted mobilities for pentacene TFTs were around 0.5 cm$^2$/Vs. The on/off ratio was 1.2×10$^5$ and the threshold voltage was −8.7 V. The n-type mobilities, on/off ratio and threshold voltage for the TC-PTCDI were 0.10 cm$^2$/Vs, 1.2×10$^5$, 4.8V. The excellent air-stability of both the p-type and n-type materials enables the organic TFTs to work very well in ambient air. As shown in FIG. 4, for $V_{dd}$=40 V, the highest gain for TC-PTCDI inverter is about 12, the noise margin is 4.5 V and the output voltage swing is about 33V. Here the output voltage swing is defined as the difference between the maximum and minimum values of the output voltage. The corresponding values are 9, 4 V, and 27 V for $V_{dd}$=30 V, and 11, 7.5 V, and 47 V for $V_{dd}$=50 V. The output voltage starts from values close to the applied voltage $V_{dd}$, and then dramatically drops to very low values. The hysteresis is shown in FIG. 5. Minor hysteresis was observed and there could be several causes for it. Both mobile charges in the gate dielectric, charge trapping at the dielectric/semiconductor interface, and/or imperfect coupling between the p- and n-channel transistors could lead to hysteresis. We did not observe any hysteresis for pentacene transistors while the n-channel transistors operating at $V_{ds}$ of 40V and 50V exhibit very small but observable hysteresis, possibly due to charge trapping at the semiconductor/insulator interface.

General Procedure for the Fabrication of Semiconductor Elements

I. Preparation of Semiconductor Substrates by Using Physical Vapor Deposition (PVD)

n-doped silicon wafers (2.5×2.5 cm, conductivity <0.004 $\Omega^{-1}$ cm) with a thermally grown oxide layer as dielectric (unit area capacity $C_i$=10 nF/cm$^2$) were used as substrates. The substrate surfaces were cleaned by rinsing with acetone followed by isopropanol. Then the substrate surfaces were modified by treating with n-octadecyltrimethoxysilane (OTS, $C_{18}H_{37}Si(OCH_3)_3$). To this end, few drops of OTS (available from Aldrich Chem. Co.) were loaded on the preheated substrate surface (about 100° C.). The desiccator was immediately evacuated (25 mm Hg) and the substrates were left under vacuum for 5 hours. Finally, the substrates were baked at 110° C. for 15 minutes, rinsed with isopropanol and dried with a stream of air. The compounds of the formula I were vacuum-deposited on the substrate surfaces as thin films having a thickness of about 40 nm. The deposition rate was 1.0 Å/s at $10^{-5}$ torr. Top-contact devices were fabricated by depositing gold source and drain electrodes onto the organic semiconductor films through a shadow mask. The channel length was 2000 μm and the channel width 200 μm. The electric characteristics of OFETs were measured by using a Keithley 4200-SCS semiconductor parameter analyzer.

II. Preparation of Semiconductor Substrates by Using Spin-Coating—Top-Contact Bottom-Gate Devices n-doped silicon wafers (2.5×2.5 cm, conductivity <0.004 $\Omega^{-1}$ cm) with a thermally grown oxide layer (300 nm) as dielectric (unit area capacity $C_i$=10 nF/cm$^2$) were used as substrates. The substrate surfaces were cleaned by rinsing with acetone followed by isopropanol. Then the substrate surfaces were modified by treating with n-octadecyltrimethoxysilane (OTS, $C_{18}H_{37}Si(OCH_3)_3$) as described above for the physical vapor deposition technique. The compounds of the formula I were spin-coated (800 rpm, 30 sec) onto the wafers as thin films. Dichloromethane, trichloromethane or tetrahydrofuran were used as solvents. Top-contact SD electrodes were deposited onto the spin-coated samples.

Example 17

The following compound

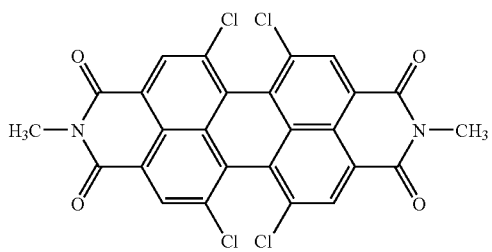

was synthesized according to known procedures and purified by three zone vacuum sublimation using a three zone furnace and processed into OFETS using vapor phase deposition according to the procedure described above. The purified material was used on an OTS pretreated substrate at 125° C. A mobility of $1.1\times10^{-3}$ cm$^2$/Vs was found.

Example 18

The following compound

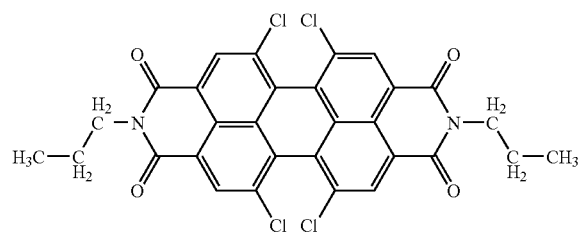

was synthesized according to known procedures and purified by three zone vacuum sublimation using a three zone furnace and processed into OFETS using vapor phase deposition according to the procedure described above. The purified material was used on an OTS pretreated substrate at 125° C. A mobility of $5.2\times10^{-4}$ cm$^2$/Vs was found.

Example 19

The following compound

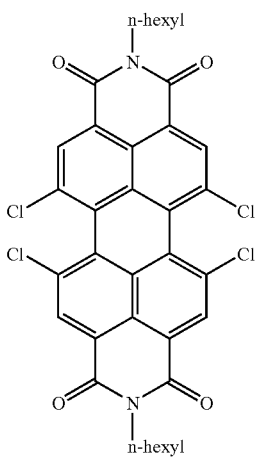

was synthesized according to known procedures and purified by three zone vacuum sublimation using a three zone furnace and processed into OFETS using vapor phase deposition according to the procedure described above. The purified material was used on an OTS pretreated substrate at 125° C. A mobility of $7.32\times10^{-3}$ cm$^2$/Vs was found.

Example 20

The following compound

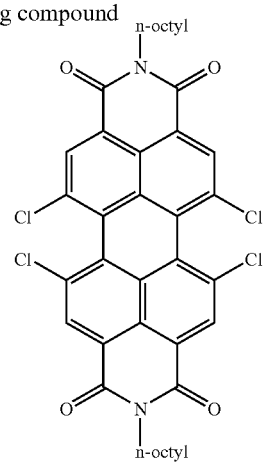

was synthesized according to known procedures and purified by three zone vacuum sublimation using a three zone furnace and processed into OFETS using vapor phase deposition according to the procedure described above. The purified material was used on an OTS pretreated substrate at 125° C. A mobility of $2.2 \times 10^{-4}$ cm$^2$/Vs was found.

Example 21

The cis/trans mixture from example 5 was purified by three zone vacuum sublimation using a three zone furnace and processed into OFETS using vapor phase deposition according to the procedure described above. The purified material was used on an OTS pretreated substrate. The following results were obtained:

| Substrate | | Room temperature | 200° C. |
|---|---|---|---|
| Inside glove box | Mobility (cm$^2$/Vs) | $3.71 \times 10^{-5}$ | $3.43 \times 10^{-4}$ |
| | on/off-ratio | ~3635 | ~34046 |
| Outside glove box | Mobility (cm$^2$/Vs) | $1.34 \times 10^{-5}$ | $5.84 \times 10^{-5}$ |
| | on/off-ratio | ~2667 | ~831 |

Example 22

The following mixture of isomers

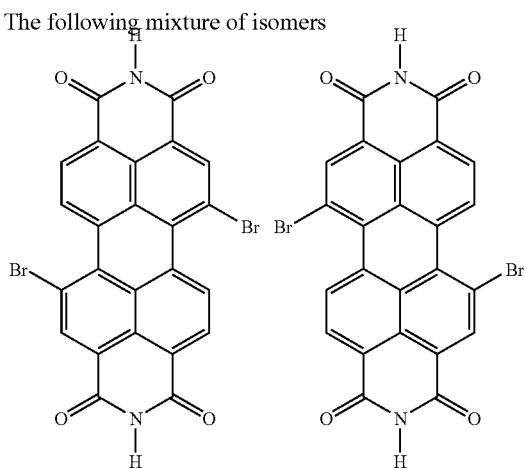

was synthesized according to known procedures and purified by three zone vacuum sublimation using a three zone furnace and processed into OFETS using vapor phase deposition according to the procedure described above. The purified material was used on an OTS pretreated substrate at 125° C. A mobility of $1.6 \times 10^{-3}$ cm$^2$/Vs was found.

Example 23

The following mixture of isomers

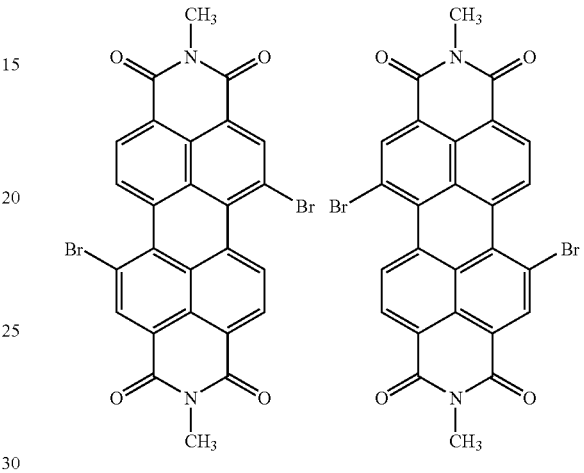

was synthesized according to known procedures and purified by three zone vacuum sublimation using a three zone furnace and processed into OFETS using vapor phase deposition according to the procedure described above. The purified material was used on an OTS pretreated substrate at 125° C. A mobility of $3.4 \times 10^{-4}$ cm$^2$/Vs was found.

Example 24

The compound from example 7 was purified by three zone vacuum sublimation using a three zone furnace and processed into OFETS using vapor phase deposition according to the procedure described above. Single Crystals were produced by physical vapour deposition and processed into OFETs according to example 11.

The obtained single crystals were employed to build an OFET on a substrate comprising a 300 nm SiO$_2$ layer as dielectric material. The obtained transistor had a W/L ratio of 9, a capacity $C_i$ of 10 nF/cm$^2$ and a mobility of $9.4 \times 10^{-4}$ cm$^2$/Vs with an on/off ratio of 4509 and the threshold voltage $V_{th}$ was 19.4 V.

OTFTs:mobility=$2 \times 10^{-5}$ cm$^2$/Vs.

Example 25

The cis/trans mixture from example 9 was purified by three zone vacuum sublimation using a three zone furnace and processed into OFETS using vapor phase deposition according to the procedure described above. The purified material was used on an OTS pretreated substrate at 125° C. A mobility of $2.1 \times 10^{-5}$ cm$^2$/Vs was found.

Example 26

The cis/trans mixture from example 10 was purified by three zone vacuum sublimation using a three zone furnace and processed into OFETS using vapor phase deposition according to the procedure described above.

The purified material was used on an OTS pretreated substrate at 125° C. A mobility of $1.1 \times 10^{-4}$ cm$^2$/Vs was found.

The purified material was also used on an OTS pretreated substrate at 150° C. A mobility of $2 \times 10^{-5}$ cm$^2$/Vs was found.

Example 27

The compound from example 7 was purified by three zone vacuum sublimation using a three zone furnace and processed into OFETS using vapor phase deposition according to the procedure described above. The purified material was used on an OTS pretreated substrate at 150° C. A mobility of $1.5 \times 10^{-5}$ cm$^2$/Vs was found.

Example 28

The compound from example 6 was purified by three zone vacuum sublimation using a three zone furnace and processed into OFETS using vapor phase deposition according to the procedure described above. The purified material was used on an OTS pretreated substrate at 150° C. A mobility of $2 \times 10^{-5}$ cm$^2$/Vs was found.

Example 29

1,6,7,12-Tetrachloroperylene-3,4:9,10-tetracarboxylic acid dianhydride (TC-PTCDA) was purified by three zone vacuum sublimation using a three zone furnace and processed into OFETS using vapor phase deposition according to the procedure described above.

The purified material was used on an OTS pretreated substrate at 80° C. A mobility of $7.0 \times 10^{-5}$ cm$^2$/Vs was found.

The purified material was used on an OTS pretreated substrate at 125° C. A mobility of $1.1 \times 10^{-4}$ cm$^2$/Vs was found Example 30

A mixture of 1,6 dibromo-3,4:9,10-perylenetetracarboxylic acid dianhydride and 1,7 dibromo-3,4:9,10-perylenetetracarboxylic acid dianhydride (DBr-PTCDA) in the ratio 15:85 was purified by three zone vacuum sublimation using a three zone furnace and processed into OFETS using vapor phase deposition according to the procedure described above.

The purified material was used on an OTS pretreated substrate at 125° C. A mobility of $7 \times 10^{-5}$ cm$^2$/Vs was found.

Example 31

The compound from example 2 was purified either by chromatography or by crystallization. The obtained material was employed to build an OFET using vapor phase deposition according to the procedure described above.

The compound from example 2, purified by chromatography was used on an OTS pretreated substrate at 150° C. A mobility of $8 \times 10^{-5}$ cm$^2$/Vs was found.

The compound from example 2, purified by crystallization was used on an OTS pretreated substrate at 150° C. A mobility of $1.8 \times 10^{-5}$ cm$^2$/Vs was found.

Example 32

N,N'-Bis(pentafluorophenyl)-1,6,7,12-tetrachloroperylene-3,4:9,10-tetracarboxylic diimide

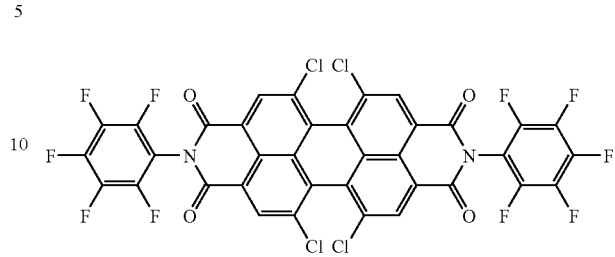

A mixture of 230 mg (0.433 mmol) of 1,6,7,12-tetrachloroperylene-3,4:9,10-tetracarboxylic acid dianhydride, 600 mg of pentafluoroaniline, 8 ml of N-methylpyrrolidone (NMP) (destillated and dry), 200 µl of acetic acid and 50 mg of zinc acetate (dried) was treated in an ultrasonic bath for 10 min and then heated under argon on 150° C. for about 10 h and further 3-4 h on 170° C. The reaction mixture was allowed to cool down to room temperature and the solid mixture was taken up in dichloromethane and poured onto 2N HCl. The reaction mixture was extracted with dichloromethane several times, the combined organic phases were dried and concentrated. The residue was purified by column chromatography using dichloromethane. Yield: 200 mg (53%).

$^1$H NMR (400 MHz, CDCl$_3$, TMS): δ=8.79 (s, 4H)

HR-MS (ESI neg.-mode, trichloromethane): 892.84628 (M+Cl$^-$), calculated: 892.84595 (C$_{36}$H$_4$Cl$_5$F$_{10}$N$_2$O$_4$);

electrochemistry: (CH$_2$Cl$_2$, 0.1M TBAHFP, vs. Ferrocen): $E^{red}_{1/2}$ (PBI/PBI$^-$)=−0.69 V
$E^{red}_{1/2}$ (PBI−/PBI$^{2-}$)=−0.89. V N,N'-Bis(pentafluorophenyl)-1,6,7,12-tetrachloroperylene-3,4:9,10-tetracarboxylic diimide was purified by three zone vacuum sublimation using a three zone furnace (T1, T2, T3) (330° C., 260° C., 194° C.), vacuum level: $1.1 \times 10^{-5}$ torr. The material used was collected from the second temperature zone (T2) after the third purification.

The compound was processed into OFETS using vapor phase deposition according to the procedure described above. The compound was used on an OTS pretreated substrate at 125° C. A mobility of 0.012 cm$^2$/Vs was found.

Air-stability measurements were carried out on thin films of N,N'-bis(pentafluorophenyl)-1,6,7,12-tetrachloroperylene-3,4:9,10-tetracarboxylic diimide (100 nm) deposited at various substrate temperatures (room temperature, 90° C., and 125° C.) on substrates treated with OTS. The following results were obtained:

| | Substrate temperature during thin film deposition | Room temperature | 90° C. | 120° C. |
|---|---|---|---|---|
| Inside Glove box | Mobility (cm$^2$/Vs) | $1.6 \times 10^{-3}$ | 0.012 | 0.022 |
| | On/off ratio | 41412 | 734515 | $1.08 \times 10^6$ |
| | $V_{th}$ (V) | 21.9 | 11.2 | 7.54 |
| Outside Glove box | Mobility (cm$^2$/Vs) | $1.5 \times 10^{-3}$ | 0.009 | 0.021 |
| | On/off ratio | 2517 | $1.17 \times 10^6$ | 275346 |
| | $V_{th}$ (V) | 27.3 | 23.5 | 38.6 |

The devices did not show a significant decrease of the initial values. This shows that N,N'-bis(pentafluorophenyl)-

1,6,7,12-tetrachloroperylene-3,4:9,10-tetracarboxylic diimide is an air-stable n-type semiconductor with good application properties.

N,N'-Bis(pentafluorophenyl)-1,6,7,12-tetrachloroperylene-3,4:9,10-tetracarboxylic diimide was also processed using the spin-coating technique according to the procedure described above. The compound was used on an OTS pretreated substrate. A mobility of $5.41 \times 10^{-5}$ cm$^2$/Vs was found.

What is claimed is:

1. A method for producing an organic field-effect transistor, comprising the steps of:
   a) providing a substrate comprising a gate structure, a source electrode and a drain electrode located on the substrate, and
   b) applying an n-type organic semiconducting compound to the area of the substrate where the gate structure, the source electrode and the drain electrode are located, wherein the n-type organic semiconducting compound is selected from compounds of the formula I

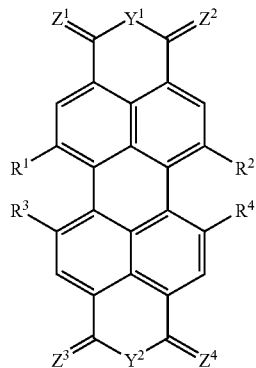

wherein
R$^1$, R$^2$, R$^3$ and R$^4$ are independently hydrogen, chlorine or bromine, with the proviso that at least one of these radicals is not hydrogen,
Y$^1$ is NR$^a$, wherein R$^a$ is hydrogen,
Y$^2$ is NR$^b$, wherein R$^b$ is hydrogen, and
Z$^1$, Z$^2$, Z$^3$ and Z$^4$ are O.

2. A method as claimed in claim 1, where 1, 2, 3 or 4 of the residues R$^1$, R$^2$, R$^3$ and R$^4$ are chlorine.

3. A method as claimed in claim 1, where R$^1$, R$^2$, R$^3$ and R$^4$ are chlorine.

4. A method as claimed in claim 1, where 1, 2, 3 or 4 of the residues R$^1$, R$^2$, R$^3$ and R$^4$ are bromine.

5. A method as claimed in claim 1, where R$^1$, R$^2$, R$^3$ and R$^4$ are bromine.

6. A method as claimed in claim 1, further comprising:
   depositing on the surface of the substrate at least one compound (C1) capable of binding to the surface of the substrate and of binding at least one organic semiconducting compound (S) of the formula I and/or at least one compound (C2) capable of binding to the surface of the substrate and preventing the binding of at least one organic semiconducting compound (S) of the formula I.

7. A method as claimed in claim 1, wherein the organic semiconducting compound of the formula I is employed in the form of crystals.

8. A method as claimed in claim 1, wherein an organic semiconducting compound of the formula I is employed that results from purification by sublimation, physical vapor transport, recrystallization from organic solvents or sulfuric acid or a combination of two or more of these methods.

9. A method for producing a crystalline n-type organic semiconducting compound comprising subjecting a compound of the formula I

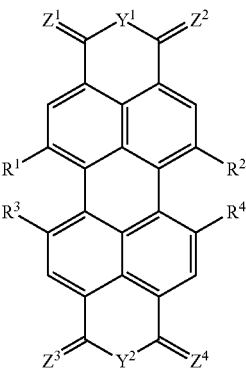

wherein
R$^1$, R$^2$, R$^3$ and R$^4$ are independently hydrogen, chlorine or bromine, with the proviso that at least one of these radicals is not hydrogen,
Y$^1$ is NR$^a$, wherein R$^a$ is hydrogen or,
Y$^2$NR$^b$, wherein R$^b$ is hydrogen or, and
Z1, Z2, Z3 and Z4 are O,
to a physical vapor transport.

10. A method for producing an electronic device, comprising:
   providing on a substrate a pattern of organic field-effect transistors, wherein at least part of the transistors comprise at least one compound of the formula I

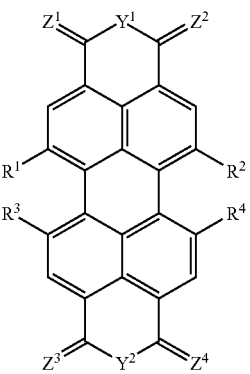

wherein
R$^1$, R$^2$, R$^3$ and R$^4$ are independently hydrogen, chlorine or bromine, with the proviso that at least one of these radicals is not hydrogen,
Y$^1$ is NR$^a$, wherein R$^a$ is hydrogen,
Y$^2$ is NR$^b$, wherein R$^b$ is hydrogen, and Z$^1$, Z$^2$, Z$^3$ and Z$^4$ are O, as n-type organic semiconducting compound.

11. An electronic device, comprising:
on a substrate, a pattern of organic field-effect transistors,
wherein at least part of the transistors comprise at least one compound of the formula

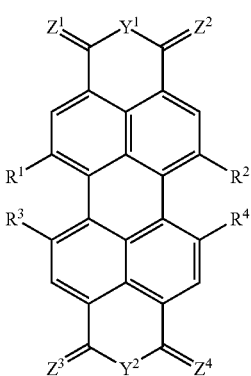

wherein
- $R^1$, $R^2$, $R^3$ and $R^4$ are independently hydrogen, chlorine or bromine, with the proviso that at least one of these radicals is not hydrogen,
- $Y^1$ is $NR^a$, wherein $R^a$ is hydrogen,
- $Y^2$ is $NR^b$, wherein $R^b$ is hydrogen, and
- $Z^1$, $Z^2$, $Z^3$ and $Z^4$ are O, as n-type organic semiconducting compound.

12. An inverter comprising at least one compound of the formula I

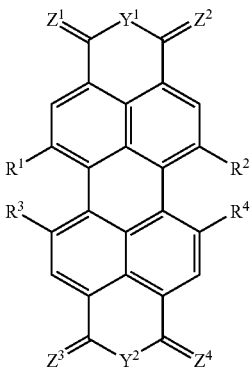

wherein
- $R^1$, $R^2$, $R^3$ and $R^4$ are independently hydrogen, chlorine or bromine, with the proviso that at least one of these radicals is not hydrogen,
- $Y^1$ is $NR^a$, wherein $R^a$ is hydrogen,
- $Y^2$ is $NR^b$, wherein $R^b$ is hydrogen, and
- $Z^1$, $Z^2$, $Z^3$ and $Z^4$ are O, as n-type organic semiconducting compound.

13. The method as claimed in claim 1, wherein compound I is selected from the group consisting of:

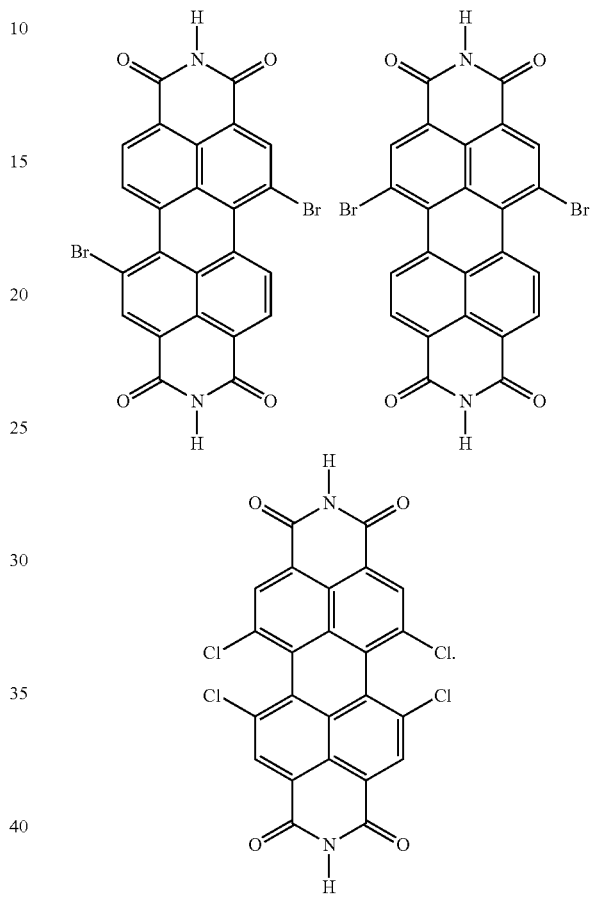

* * * * *